(12) United States Patent
Saffari

(10) Patent No.: US 12,070,400 B2
(45) Date of Patent: Aug. 27, 2024

(54) ENDOLUMINAL PROSTHESIS SYSTEMS AND METHODS

(71) Applicant: Endololgix LLC, Irvine, CA (US)

(72) Inventor: Payman Saffari, Irvine, CA (US)

(73) Assignee: Endologix LLC, Irvine, CA (US)

(*) Notice: Subject to any disclaimer, the term of this patent is extended or adjusted under 35 U.S.C. 154(b) by 0 days.

(21) Appl. No.: 17/983,259

(22) Filed: Nov. 8, 2022

(65) Prior Publication Data

US 2023/0138365 A1 May 4, 2023

Related U.S. Application Data

(63) Continuation of application No. 15/737,223, filed as application No. PCT/US2016/039414 on Jun. 24, 2016, now Pat. No. 11,497,635.

(Continued)

(51) Int. Cl.
*A61F 2/89* (2013.01)
*A61F 2/88* (2006.01)
*A61F 2/915* (2013.01)

(52) U.S. Cl.
CPC ............. *A61F 2/89* (2013.01); *A61F 2/88* (2013.01); *A61F 2/915* (2013.01); *A61F 2002/91533* (2013.01); *A61F 2002/91566* (2013.01); *A61F 2002/91575* (2013.01); *A61F 2210/0014* (2013.01); *A61F 2210/0071* (2013.01); *A61F 2230/0054* (2013.01); *A61F 2250/0037* (2013.01)

(58) Field of Classification Search
CPC .... A61F 2/89; A61F 2/88; A61F 2/915; A61F 2002/91566; A61F 2230/0054; A61F 2250/0037
See application file for complete search history.

(56) References Cited

U.S. PATENT DOCUMENTS

| | | |
|---|---|---|
| 5,907,893 A | 6/1999 | Zadno-Azizi et al. |
| 7,018,403 B1 | 3/2006 | Pienknagura |

(Continued)

FOREIGN PATENT DOCUMENTS

| | | |
|---|---|---|
| CN | 103313681 A | 9/2013 |
| JP | 2001-509702 A | 7/2001 |
| WO | WO-2015/070124 A2 | 5/2015 |

OTHER PUBLICATIONS

Chinese Office Action dated Apr. 2, 2019, from application No. 201680037099.X.

(Continued)

*Primary Examiner* — Anh T Dang
(74) *Attorney, Agent, or Firm* — Foley & Lardner LLP

(57) ABSTRACT

A stent includes a main body having a plurality of rings that form a helix. Each of the plurality of rings includes a plurality of skewed v-shaped elements that each have a first leg and a second leg that is longer than the first leg. The stent further includes a first end ring and a second end ring positioned to an opposite side of the main body from the first end ring. Each of the plurality of rings of the main body is angled with respect to the first end ring and the second end ring. The stent further includes a first transitional region for connecting the first end ring to the main body, and a second transitional region for connecting the second end ring to the main body.

20 Claims, 18 Drawing Sheets

Related U.S. Application Data

(60) Provisional application No. 62/183,735, filed on Jun. 24, 2015.

(56) References Cited

U.S. PATENT DOCUMENTS

| | | | |
|---|---|---|---|
| 8,038,707 | B2 | 10/2011 | Bales et al. |
| 8,500,793 | B2 | 8/2013 | Zipse et al. |
| 8,834,554 | B2 | 9/2014 | Ta |
| 2003/0033003 | A1 | 2/2003 | Harrison et al. |
| 2004/0044400 | A1 | 3/2004 | Cheng et al. |
| 2004/0093073 | A1 | 5/2004 | Lowe et al. |
| 2004/0102834 | A1 | 5/2004 | Nakano et al. |
| 2004/0249445 | A1 | 12/2004 | Rosenthal et al. |
| 2007/0250148 | A1* | 10/2007 | Perry, Jr. ............... A61F 2/915 623/1.22 |
| 2008/0154354 | A1 | 6/2008 | Kveen et al. |
| 2010/0016949 | A1* | 1/2010 | Wack ...................... A61F 2/92 623/1.15 |
| 2010/0298921 | A1 | 11/2010 | Schlun et al. |
| 2011/0160833 | A1 | 6/2011 | Gonzalez et al. |
| 2011/0166641 | A1 | 7/2011 | Bales et al. |
| 2011/0245910 | A1 | 10/2011 | Beach et al. |
| 2013/0197617 | A1 | 8/2013 | Armstrong et al. |
| 2013/0289707 | A1 | 10/2013 | Shanley et al. |

OTHER PUBLICATIONS

Chinese Office Action dated Feb. 27, 2020, from application No. 201680037099.X.
Chinese Office Action dated Mar. 30, 2021, from application No. 201680037099.X.
Chinese Office Action dated Sep. 15, 2020, from application No. 201680037099.X.
European Office Action dated Aug. 17, 2022, from application No. 16815450.8.
European Office Action dated Mar. 31, 2021, from application No. 16815450.8.
Extended European Search Report dated Jan. 22, 2019, from application No. 16815450.8.
International Preliminary Report on Patentability dated Jan. 4, 2018, from international application No. PCT/US2016/039414.
International Search Report and Written Opinion dated Sep. 8, 2016, from international application No. PCT/US2016/039414.
Japanese Office Action dated Jun. 2, 2020, from application No. 2017-566745.
US Final Office Action dated Feb. 20, 2020, from U.S. Appl. No. 15/737,223.
US Final Office Action dated Mar. 4, 2021, from U.S. Appl. No. 15/737,223.
US Non-Final Office Action dated Jun. 1, 2020, for U.S. Appl. No. 15/737,223.
US Non-Final Office Action dated Oct. 15, 2021, for U.S. Appl. No. 15/737,223.
US Non-Final Office Action dated Sep. 25, 2019, for U.S. Appl. No. 15/737,223.
US Notice of Allowance dated Jul. 18, 2022, for U.S. Appl. No. 15/737,223.

* cited by examiner

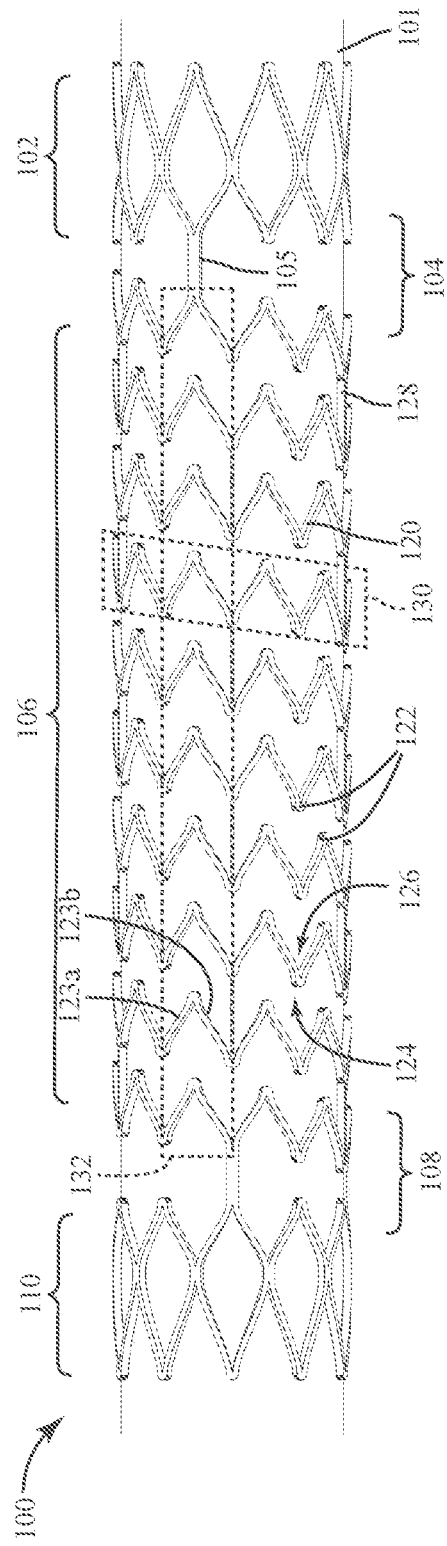
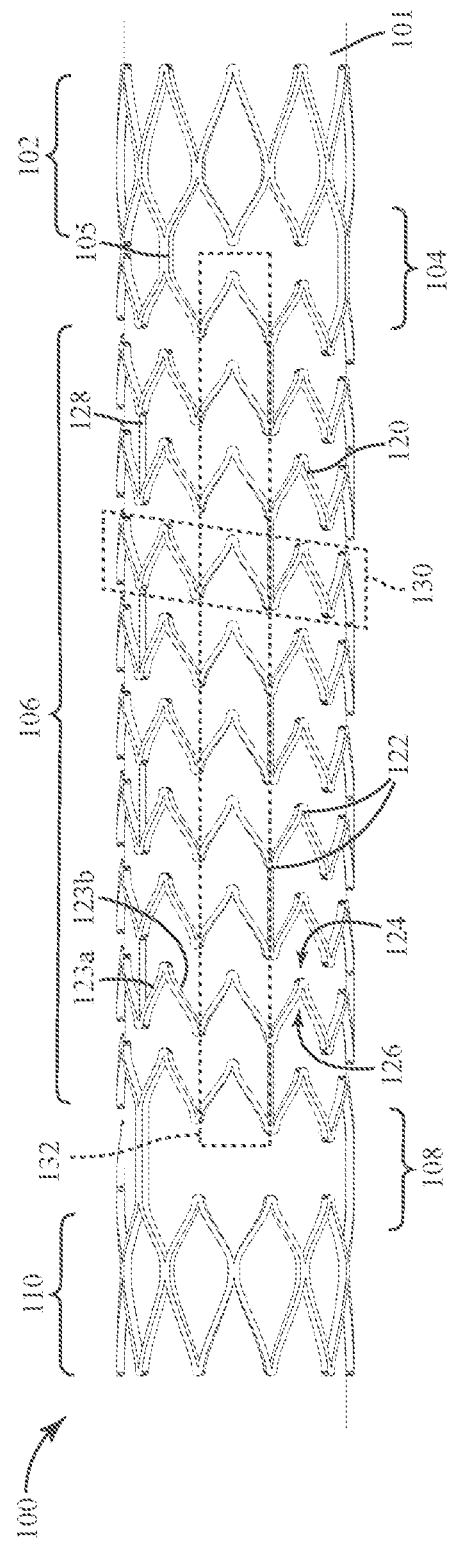
Fig. 7
Fig. 8

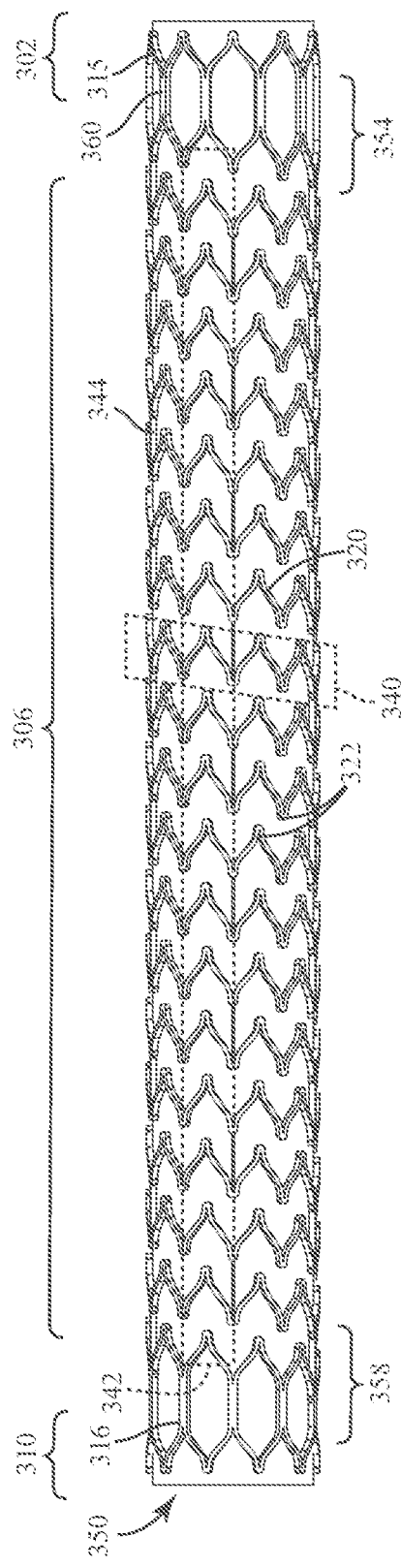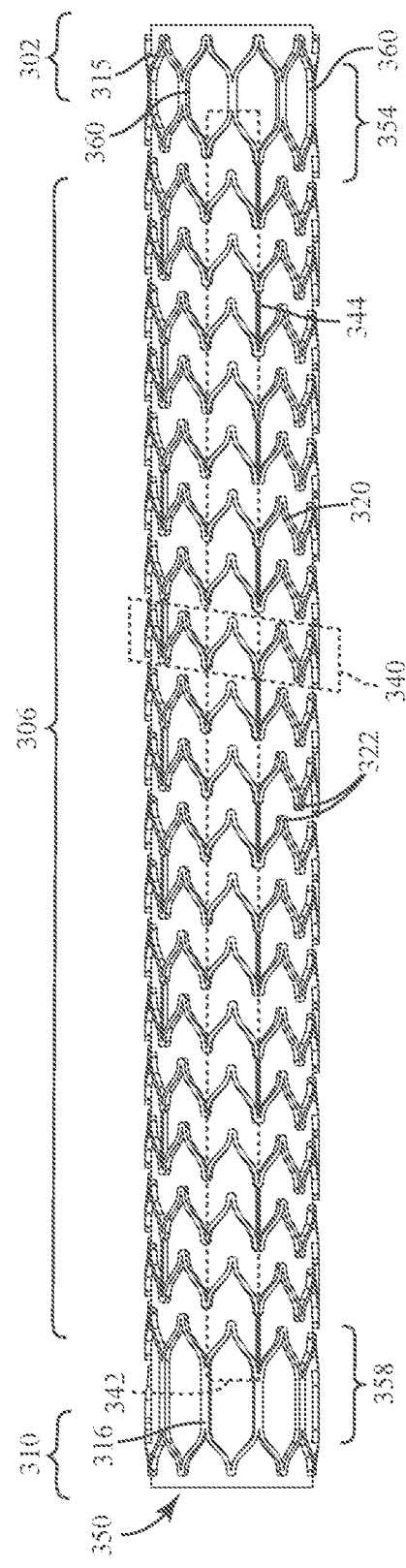
Fig. 19
Fig. 20

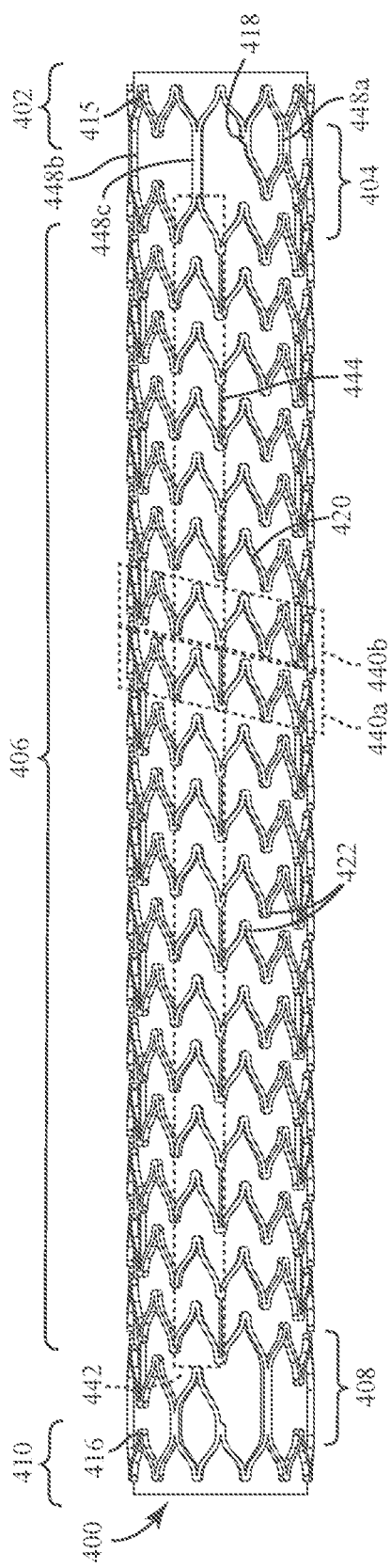
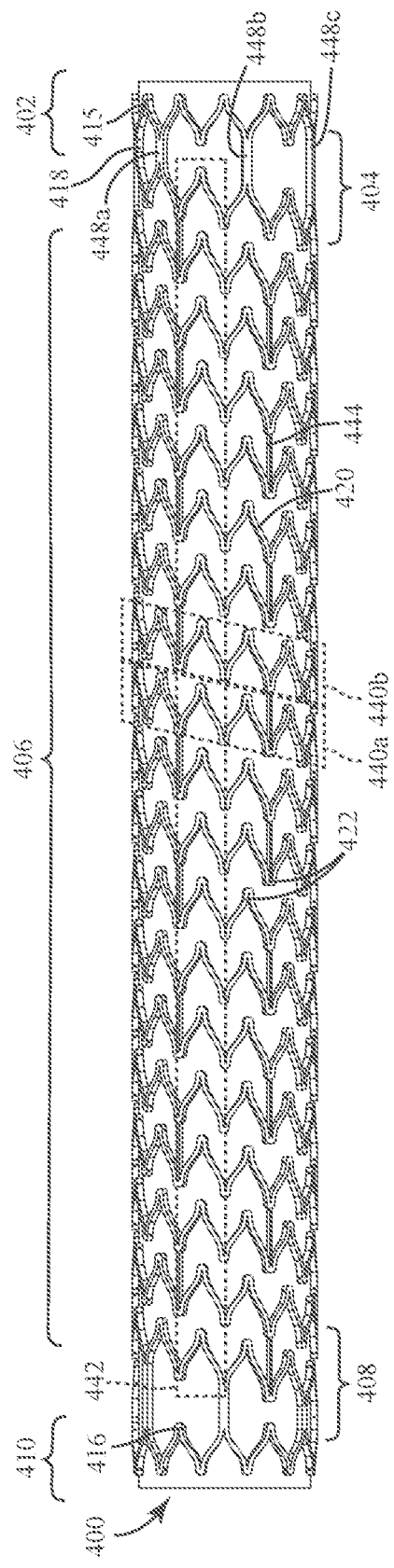
Fig. 24
Fig. 25

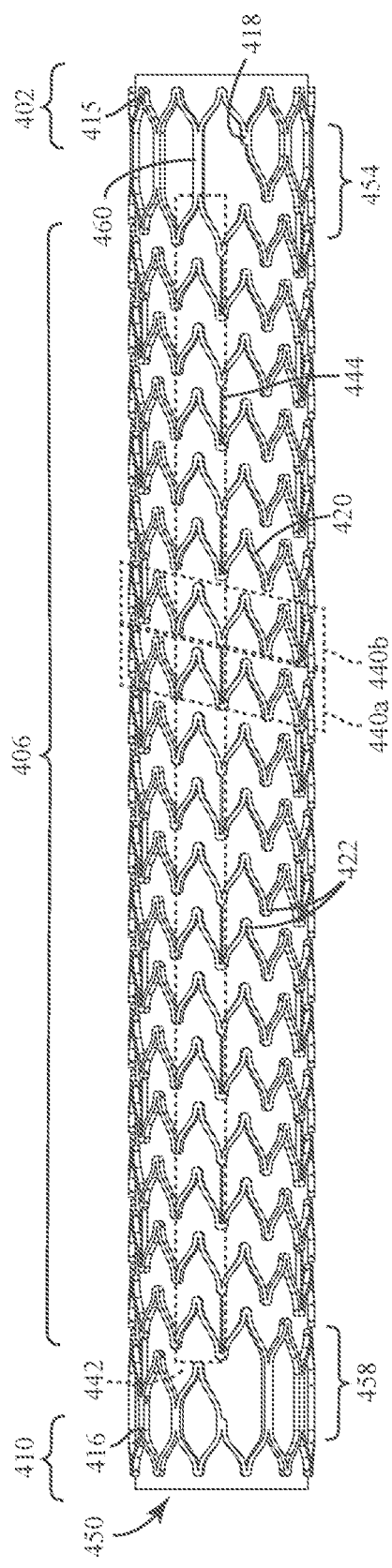

ENDOLUMINAL PROSTHESIS SYSTEMS AND METHODS

CROSS-REFERENCE TO RELATED PATENT APPLICATIONS

This application is a continuation of U.S. patent application Ser. No. 15/737,223, filed Dec. 15, 2017, which is a U.S. National Stage Application under 35 U.S.C. § 371 of International Application No. PCT/US2016/039414, filed Jun. 24, 2016, which claims priority from U.S. Provisional Patent App. Ser. No. 62/183,735, filed Jun. 24, 2015, the entire contents of each of which are incorporated by reference herein.

FIELD

Various embodiments disclosed herein relate generally to medical apparatuses and methods for treatment of arterial disease. More particularly, various embodiments relate to expandable prostheses and methods for treating abdominal and other aneurysms. Various embodiments relate to devices and methods of treating an abdominal, paravisceral, juxtarenal, peripheral, or thoracic aneurysms.

BACKGROUND

Aneurysms are enlargements or bulges in blood vessels that are often prone to rupture and which therefore present a serious risk to a patient. Aneurysms may occur in any blood vessel but are of particular concern when they occur in the cerebral vasculature or the patient's aorta.

Some embodiments of the present disclosure are concerned with aneurysms occurring in the aorta, particularly those referred to as aortic aneurysms. Abdominal aortic aneurysms (AAA's) are classified based on their location within the aorta as well as their shape and complexity. Aneurysms that are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about seventy percent (70%) of all aortic aneurysms. Suprarenal aneurysms are less common, representing about twenty percent (20%) of the aortic aneurysms. Thoracic aortic aneurysms are the least common and often the most difficult to treat. Many endovascular systems are also too large (above 4 mm in diameter) for percutaneous introduction.

The most common form of aneurysm is fusiform, wherein the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Endoluminal grafts can be used for the treatment of aortic aneurysm in patients who cannot undergo open surgical procedures. In general, endoluminal repairs access the aneurysm endoluminally through either or both iliac arteries in the groin. Subclavian access is also used to perform branched procedures. The grafts, which can have fabric or membrane tubes supported and attached by various stent structures, are then implanted, and can require several pieces or modules to be assembled in situ. Successful endoluminal procedures can have a much shorter recovery period than open surgical procedures.

Many designs of helical stents for treating aneurysms require a lot of manual work during the manufacturing process in order to align and adjust the struts of the stent to achieve uniform geometry pattern. Helical stents when expanded may lengthen or foreshorten causing unpredictability in placement of the stent relative to an anatomy. Many times the branches associated with an aneurysm may also need to be stented. Aneurysms in the aorta may require that various branches, such as but not limited to renal arties, iliac arteries, the superior mesenteric artery (SMA), and the celiac artery be partially stented. Branched stents for repairing such branches often face challenges with respect to lacking enough flexibility to withstand the physiological motion of the branch vessels.

SUMMARY OF THE DISCLOSURE

A stent includes a main body having a plurality of rings that form a helix. In various embodiments, each of the plurality of rings includes a plurality of skewed v-shaped elements that each have a first leg and a second leg that is longer than the first leg. In various embodiments, the stent further includes an end ring, and a ring of the plurality of rings of the main body is angled with respect to the end ring. In some embodiments, the end ring is shaped to have a plurality of peaks of the end ring, and the skewed v-shaped elements and the connections between the skewed v-shaped elements in the ring of the plurality of rings of the main body form a plurality of peaks of the ring. In various embodiments, the stent further comprises a transition region including one or more struts, and each of the one or more struts connects a corresponding peak of the plurality of peaks of the end ring to a corresponding peak of the plurality of peaks of the ring.

In some embodiments, the stent includes a transition region including a first strut for connecting the end ring to the ring and a second connecting strut for connecting the end ring to the ring, where a length of the second strut is longer than a length of the first strut. In some embodiments, the transition region further includes a third strut for connecting the end ring to the ring, and a length of the third strut is longer than the length of the second strut. In some embodiments, a distance between the second strut and the third strut is greater than a distance between the first strut and the second strut.

In various embodiments, the stent includes a plurality of connecting struts for connecting a ring of the plurality of rings of the main body with an adjacent ring of the plurality of rings of the main body. In some embodiments, each of the plurality of connecting struts extends from a corresponding peak of a plurality of peaks of the ring to a corresponding valley of a plurality of valleys of the adjacent ring. In some embodiments, a distance between each of the plurality of connecting struts is greater than a width of a skewed v-shaped element of the plurality of skewed v-shaped elements. In some embodiments, a distance between each of the plurality of connecting struts is greater than double a width of a skewed v-shaped element of the plurality of skewed v-shaped elements.

In various embodiments, the stent further includes a first plurality of connecting struts for connecting a ring of the plurality of rings of the main body with a first adjacent ring of the plurality of rings of the main body, and a second plurality of connecting struts for connecting the ring with a second adjacent ring of the plurality of rings of the main body. In some embodiments, each of the first plurality of connecting struts extends from a corresponding peak of a plurality of peaks of the ring to a corresponding valley of a plurality of valleys of the first adjacent ring, and each of the second plurality of connecting struts extends from a corresponding valley of a plurality of valleys of the ring to a corresponding peak of a plurality of peaks of the second adjacent ring.

In various embodiments, a particular connecting strut of the second plurality of connecting struts is equidistant from a corresponding two connecting struts of the first plurality of connecting struts that are nearest to the particular connecting strut. In some embodiments, the first leg and the second leg of each of the plurality of skewed v-shaped elements of each of the plurality of rings have respective lengths such that there is a group of v-shaped elements that have corresponding apices aligned with each other in a direction that is parallel to a longitudinal axis of the stent.

In various embodiments, the main body further comprises a second plurality of rings that form a second helix. Also, in various embodiments, an end ring of the stent includes a plurality of tear drop shaped elements, and the stent further includes a transition region connecting a peak of a tear drop shaped element of the plurality of tear drop shaped elements of the end ring to the main body.

In some embodiments, the stent includes a first end ring and a second end ring positioned to an opposite side of the main body from the first end ring, and each of the plurality of rings of the main body is angled with respect to the first end ring and the second end ring. In some embodiments, a width direction of an end of the first end ring and a width direction of an end of the second end ring are perpendicular to a longitudinal axis of the stent. In some embodiments, the stent includes a first transitional region for connecting the first end ring to the main body, and a second transitional region for connecting the second end ring to the main body. In various embodiments, the stent further includes a plurality of connecting struts extending between rings of the plurality of rings, where each of the plurality of connecting struts is arranged parallel to a longitudinal axis of the stent.

BRIEF DESCRIPTION OF THE DRAWINGS

FIG. 7 is a rear orthogonal view of the endoluminal prosthesis of FIG. 1.

FIG. 8 is a bottom orthogonal view of the endoluminal prosthesis of FIG. 1.

FIG. 19 is a rear orthogonal view of the endoluminal prosthesis of FIG. 16.

FIG. 20 is a bottom orthogonal view of the endoluminal prosthesis of FIG. 16

FIG. 24 is a rear orthogonal view of the endoluminal prosthesis of FIG. 21.

FIG. 25 is a bottom orthogonal view of the endoluminal prosthesis of FIG. 21.

FIG. 27 is a front orthogonal view of the endoluminal prosthesis of FIG. 26.

FIG. 28 is a top orthogonal view of the endoluminal prosthesis of FIG. 26.

DETAILED DESCRIPTION

Figure 1:
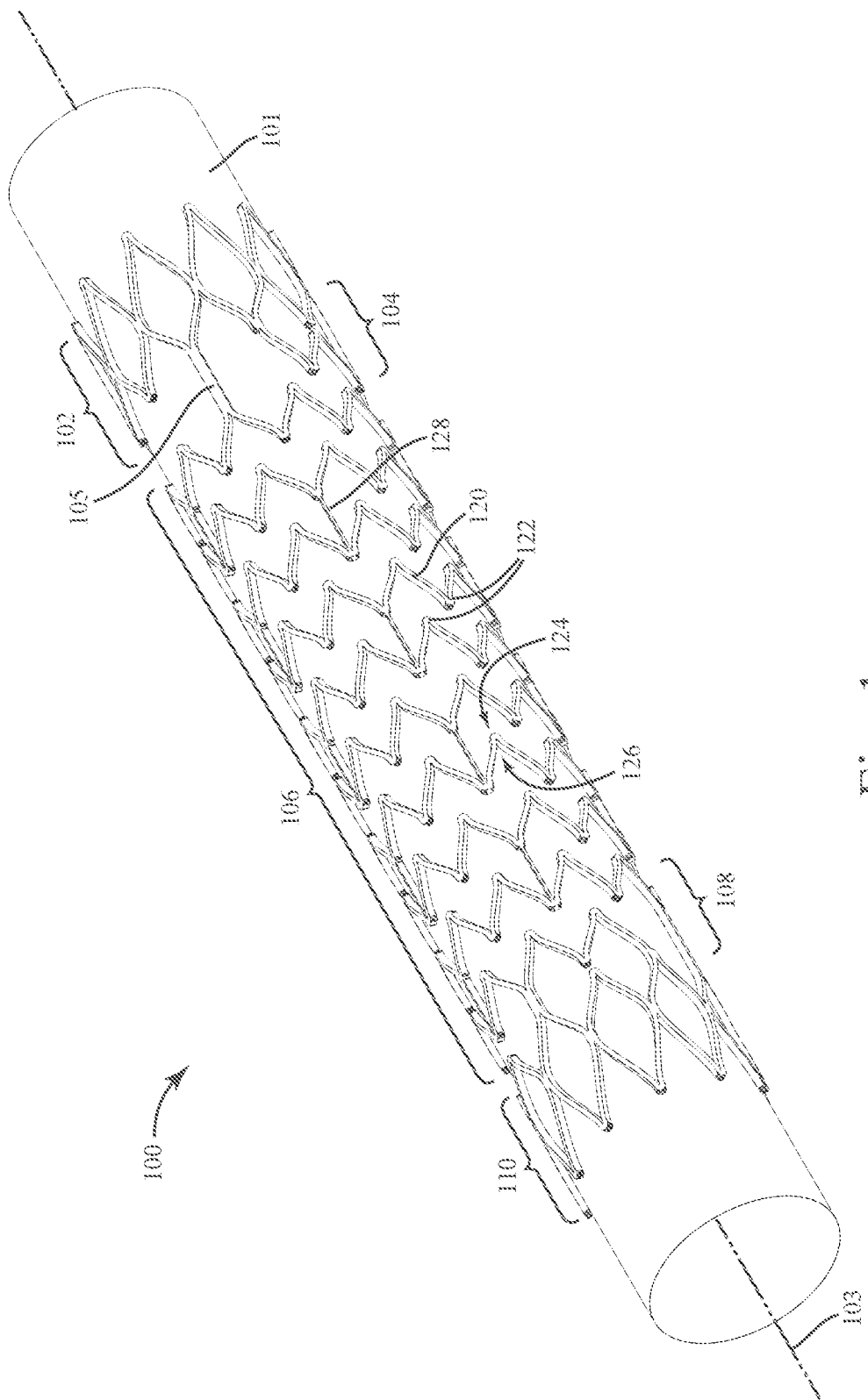
FIG. 1 is a perspective view of an endoluminal prosthesis according to an embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Referring to FIGS. 1, 2, 3, 4, 5, 6, 7, and 8, a stent 100 is shown in accordance with an embodiment. In various views, the stent 100 is shown surrounding an exemplary mandrel 101 for ease of illustration. The stent 100 includes a first end ring 102, a first transition region 104, a main body 106, a second transition region 108, and a second end ring 110. The stent 100 defines a longitudinal axis 103. The stent 100 may be deployed in any blood vessel, including unbranched and branched blood vessels. In some embodiments, the various features of the stent 100 enhance the performance of the stent 100 for branched vessel applications. In various embodiments, the stent 100 is formed from a suitable biocompatible material, such as a biocompatible alloy, a biocompatible metal, or a biocompatible polymer that may be a thermoplastic material. In some embodiments, the stent 100 is formed from a steel, cobalt chromium, nitinol, and/or shape memory alloy. The stent 100 may be configured with an expandable geometry. For example, in some embodiments, the stent 100 is a self-expanding stent. In some embodiments, the stent 100 is a balloon-expandable stent.

Figure 2:
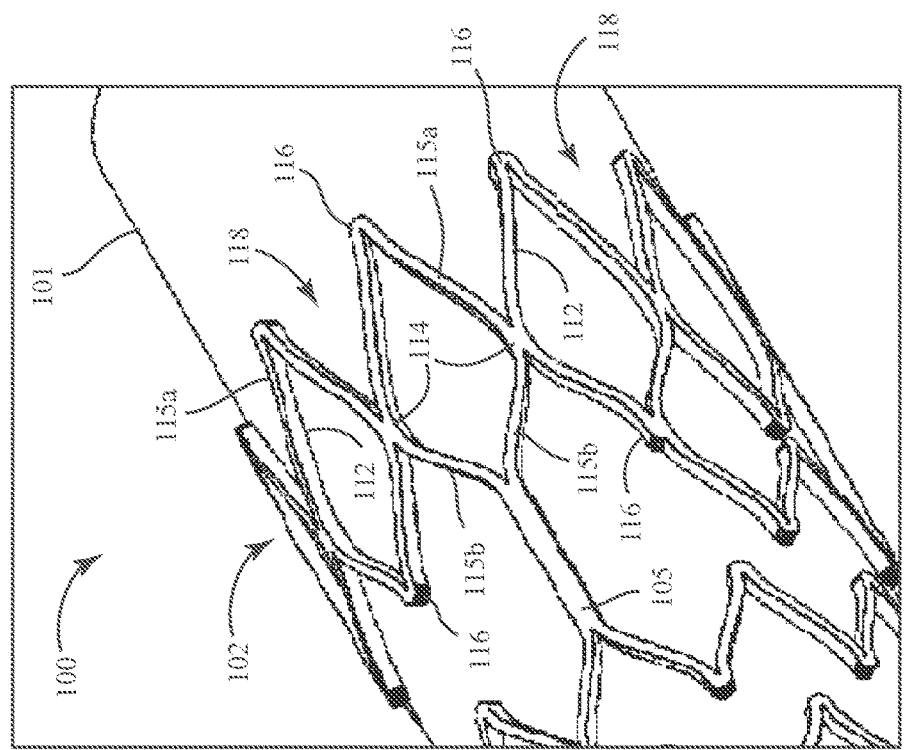
FIG. 2 is a perspective view of an end ring of the endoluminal prosthesis of FIG. 1.
Figure 3:
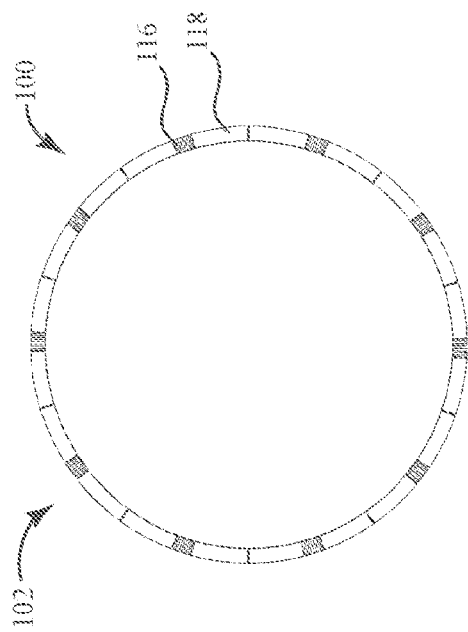
FIG. 3 is a right orthogonal view of the endoluminal prosthesis of FIG. 1.
Figure 4:
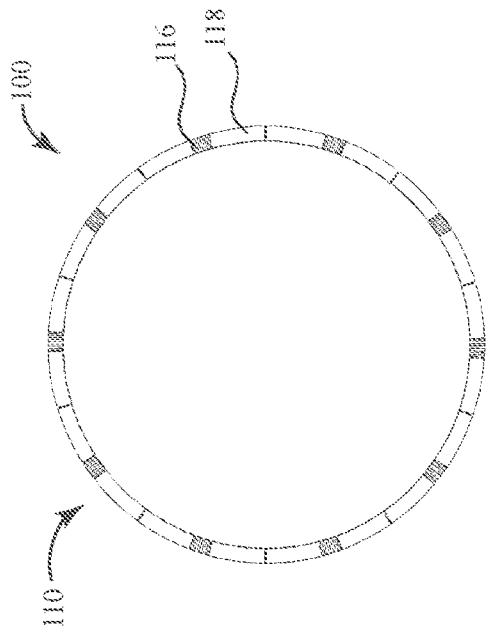
FIG. 4 is a left orthogonal view of the endoluminal prosthesis of FIG. 1.
Figure 5:
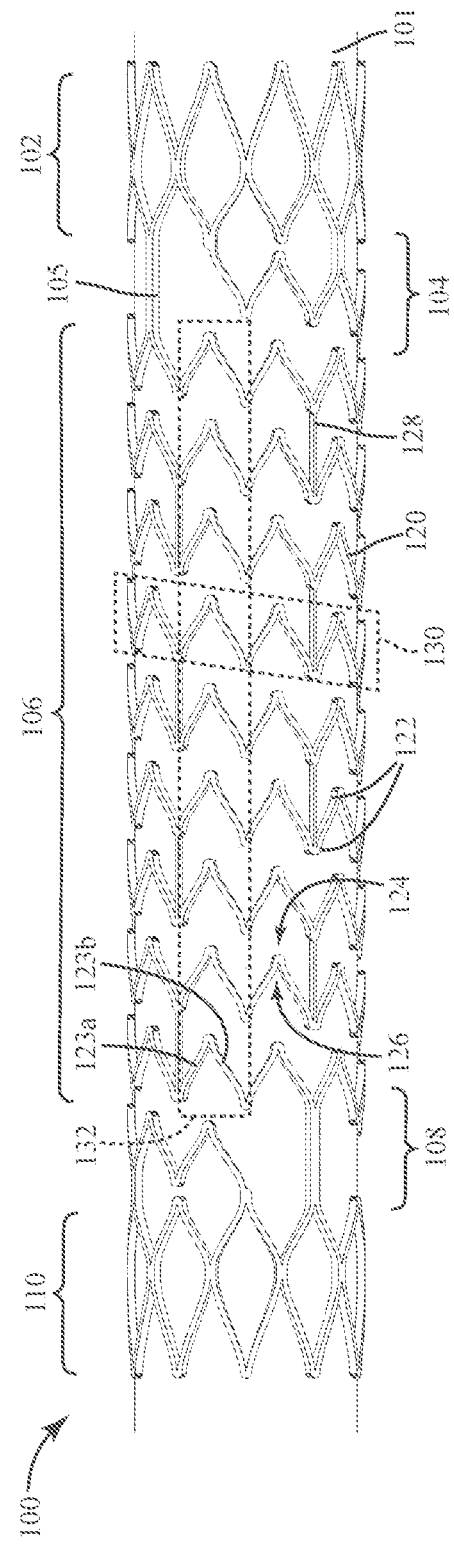
FIG. 5 is a front orthogonal view of the endoluminal prosthesis of FIG. 1.
Figure 6:
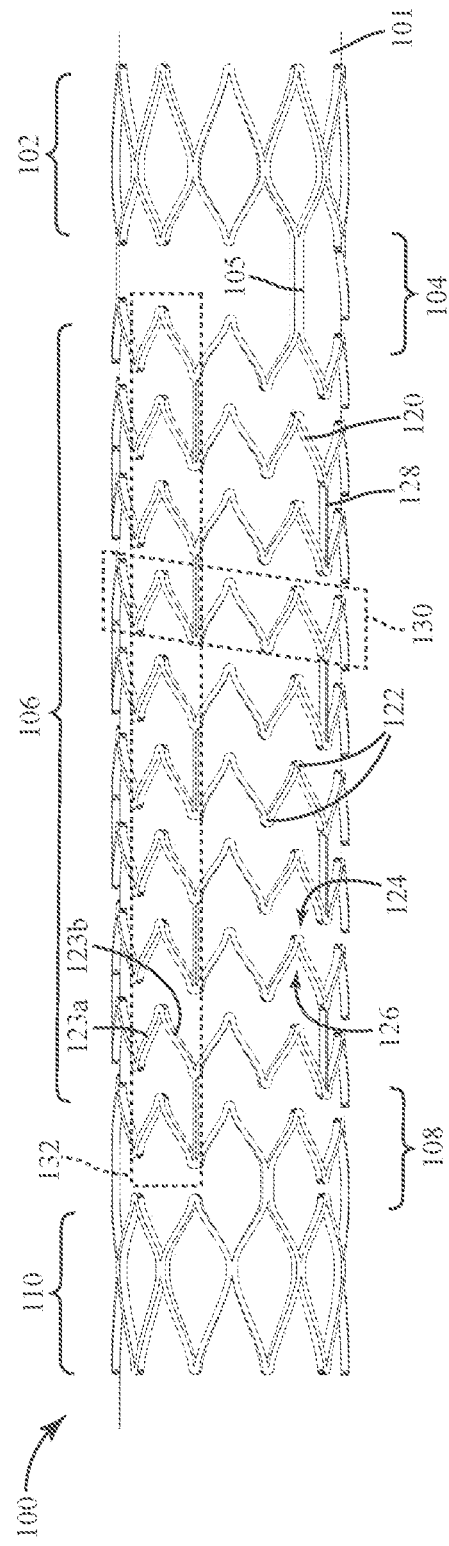
FIG. 6 is a top orthogonal view of the endoluminal prosthesis of FIG. 1.

Referring to FIGS. 2 and 3, the first end ring 102 is shown in more detail, and referring to FIG. 4, the second end ring 110 is shown in more detail. With reference to FIGS. 1, 2, 3, and 4, the first and second end rings 102 and 110 are shown to be similar in construction. According to an exemplary embodiment, the first and second end rings 102 and 110 may be formed from elements 112 having a tear drop shape spaced about the circumference of the stent 100. Each of the tear drop shaped elements 112 is coupled to others of the tear drop shaped elements 112 on either side via a joint 114 at the widest portion of the tear drop shaped elements 112 to form a complete ring, as shown in FIG. 2. In some embodiments, the tear drop shaped elements 112, when coupled together at the joints 114, form v-shaped elements 115a and 115b. Each of the v-shaped elements 115a and 115b have an end or apex 116. As shown in FIG. 2, the tear drop shaped elements 112 each include a first, outwardly pointed v-shaped element 115a and a second, inwardly-pointed v-shaped element 115b, with the v-shaped elements 115a and 115b joined together at the joints 114. There is a space 118 between the apex 116 of each of the v-shaped elements 115a. In an exemplary embodiment, the v-shaped elements 115a and 115b are formed such that the arms of the v-shaped elements 115a and 115b are roughly sinusoidal in shape due to the construction of the stent 100 with a laser-cutting and expansion process. In other embodiments, the v-shaped elements 115a and 115b are formed such that the arms of the v-shaped elements 115a and 115b are otherwise shaped, such as straight, convex, concave, or the like.

In various embodiments, the two types of v-shaped elements 115a and 115b may be of different sizes. For example, the outwardly-pointing v-shaped elements 115a may have legs that are longer than legs of the inwardly-pointed v-shaped elements 115b, thus resulting in the tear drop shaped elements 112. In other embodiments, each of the end portions 102 and 110 include a plurality of diamond-shaped elements that each include two relatively similarly sized v-shaped elements spaced about the circumference of the stent 100 with each of the diamond-shaped elements being coupled to diamond-shaped elements on either side via a joint at the widest portion of the diamond-shaped elements. In some embodiments, the end portions 102 and 110 may include elements comprising only inwardly-pointed v-shaped elements 115b. In some embodiments, one or both of the end portions 102 and 110 may be otherwise shaped.

Referring to FIGS. 1 and 2, the first transition region 104 and the second transition region 108 transition from the end rings 102 and 110, respectively, to the helical shaped main body 106. The first transition region 104 couples the first end ring 102 to the main body 106 and, on the other end of the stent 100, the second transition region 108 connects the second end ring 110 to the main body 106. The transition regions 104 and 108 may include one or more bridges or struts 105 that connect a corresponding apex 116 from the first end ring 102 or the second end ring 110 to a peak of an adjacent helical ring of the main body 106. Because a helical ring of the main body 106 is angled relative to the end rings 102 and 110, the distance between the main body 106 and the end rings 102 and 110 that is spanned by the struts 105 varies about the circumference of the stent 100. Accordingly, the lengths of the struts 105 that connect the end rings 102 and 110 to the main body 106 may vary from one another. In some embodiments, the helically shaped main body 106 may be coupled directly to one of the apices 116 of the end rings 102 and 110.

In some embodiments, the transition regions 104 and 108 may include three bridges or struts 105 that are variably spaced apart from each other. For example, the distance between bridges or struts 105 may increase by a distance equal to the width of one of the elements 112 of the end rings 102 and 110. The transition regions 104 and 108 between the main body 106 and the end rings 102 and 110 may include a peak-to-peak connection, such as with the struts 105 extending between an apex 116 of the end ring 102 or 110 to an apex of the main body 106 to provide more stability to the end rings 102 and 110 and enable uniform expansion and contraction of the stent 100. It is to be understood that the transition region 108 may be similar in construction to the transition region 104 or may vary in construction compared to the transition region 104. For example, the transition region 108 may include more or fewer struts 105 compared to the transition region 104.

Referring now to FIGS. 1, 5, 6, 7, and 8, the main body 106 of the stent 100 includes helical rings 130 formed from v-shaped elements 120. The v-shaped elements 120 are sized such that the elements 120 of each loop or ring 130 of the helix are aligned with the elements 120 of an adjacent ring 130. Each ring 130 is angled relative to an axis perpendicular to the longitudinal axis of the stent 100. The angle of each ring 130 may vary based on the design of the stent 100.

Each of the v-shaped elements 120 is coupled to v-shaped elements 120 on either side via a joint, forming an apex 122. The v-shape of each of the v-shaped elements 120 also forms an apex 122 at the middle portion of the v-shape. A first side of each apex 122 defines a peak 124 and a second, opposite side of the apex 122 defines a valley 126. Each of the v-shaped elements 120 is skewed such that a first leg 123a of the v-shaped element 120 is shorter than a second leg 123b of the v-shaped element 120. Because each of the v-shaped elements 120 are skewed with the shorter first leg 123a and the longer second leg 123b, each of the groups 132 of v-shaped elements 120 on neighboring rings 130 that are aligned along a direction parallel to the longitudinal axis 103 of the stent 100 are aligned as a group parallel to the longitudinal axis 103 of the stent 100.

In some embodiments, v-shaped elements 120 of neighboring loops 130 of the main body 106 are connected to each other with connecting struts 128, where each connecting strut 128 extends from the peak 124 of a corresponding apex 122 on one ring 130 of the helix to the valley 126 of another corresponding apex 122 of another ring 130 of the helix for the stent 100. The connecting struts 128 maintain the shape of the main body 106 of the stent 100 with the apices 122 of one ring 130 aligned with the corresponding apices 122 of the neighboring ring 130 in a direction parallel to the longitudinal axis 103 of the stent 100, ensuring that peaks are nested in the center of the neighboring valleys, in some embodiments. Clearance is therefore provided for the v-shaped elements 120 to bend and flex, granting a great amount of flexibility to the main body 106 of the stent 100. The connecting struts 128 maintain this alignment even when the main body 106 of the stent 100 is bent at a relatively large angle.

Each apex 122 of the v-shaped elements 120 forming the main body 106 may initiate and receive connecting struts 128 that connect to corresponding apices 122 of the v-shaped elements 120 of the adjacent ring. In various embodiments, the frequency of connecting struts 128 and the ratio apices 122 joined by connecting struts 128 versus free apices may vary. In some embodiments, the connecting struts 128 are spaced such that four v-shaped elements 120 are provided between each connecting strut 128. In various embodiments, it is possible to have 1, 2, 3, 4, 5, 6, 7, or any other suitable number of v-shaped elements 120 between each connecting strut 128. In some embodiments, every third v-shaped element 120 in a ring 130 has a connecting strut 128 to an adjacent ring 130. Increasing the number of connections between rings 130 with the connecting struts 128 may decrease the flexibility of the endoluminal prosthesis, and conversely decreasing the number of connections between rings 130 with the connecting struts 128 may increase the flexibility of the endoluminal prosthesis.

The peak-to-valley arrangement of the connecting struts 128 allows the stent 100 to radially expand and contract in a uniform manner. Uniform radial expansion and contraction may lead to easier manufacturing, more uniform deployed shape, and better wall apposition. The peak-to-valley arrangement of the connecting struts 128 arranges the apices 122 of the v-shaped elements 120 to be aligned with each other in the direction parallel to the longitudinal axis 103 of the stent 100 during radial expansion/contraction of the stent 100.

In various embodiments the helical configuration of the main body 106 provides additional flexibility for the bending of the stent 100 when a portion of the stent 100 is placed within a branch vessel originating in a larger vessel and the other portion is placed at an angle greater than or equal to ninety degrees in the larger vessel, such as but not limited to the aorta. Accordingly, the helical pattern of the main body 106 disclosed herein may allow the stent 100 to achieve more flexibility than other designs while retaining patency or blood flow to the organs through the larger vessel and the branch vessel.

Figure 9:
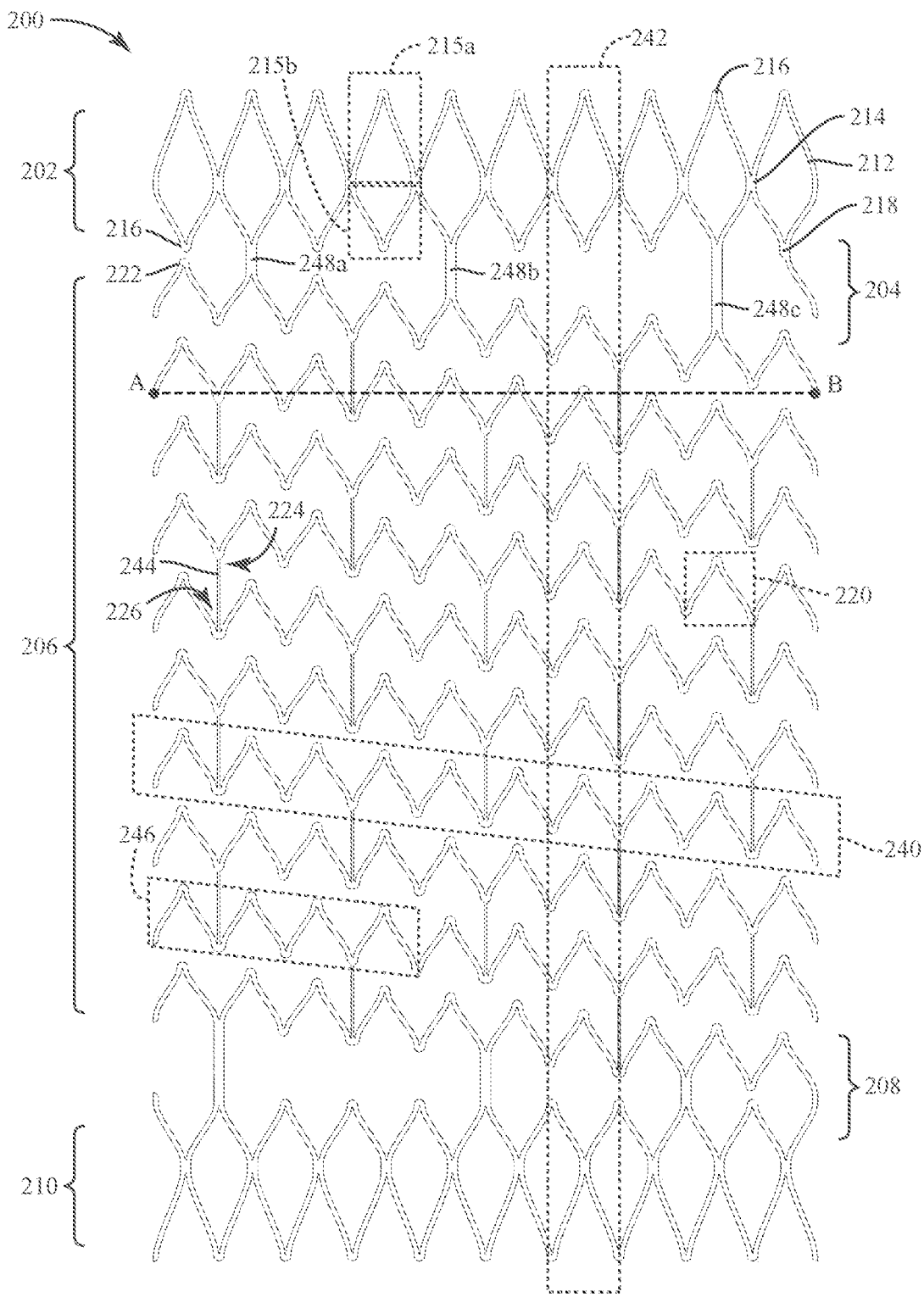
FIG. 9 is a flat view of an endoluminal prosthesis, according to an exemplary embodiment.

Referring to FIG. 9, a flat view of a stent 200 is shown in accordance with an embodiment. The stent 200 may be similar in shape to the stent 100 discussed above with reference to FIGS. 1-8. The stent 200 includes a first end ring 202, a first transition region 204, a main body 206, a second transition region 208 and a second end ring 210. While the stent 200 is generally manufactured to be a generally cylindrical body, the flat view illustrated in FIG. 9 is provided for clarity. End points on one side of the stent 200, as shown by point A are understood to be continuous with corresponding end points on the opposite side of the stent 200, as shown by point B.

The end rings 202 and 210 are formed from tear drop shaped elements 212. Each of the tear drop shaped elements 212 is coupled to corresponding tear drop shaped elements 212 on either side via a joint 214 at the widest portion of the tear drop shaped elements 212 to form a complete ring. In some embodiments, each of the tear drop shaped elements 212 are formed by v-shaped elements 215a and 215b that each have an apex 216. As shown in FIG. 9, the tear drop shaped elements 212 each include a first, outwardly-pointed v-shaped element 215a and a second, inwardly-pointed v-shaped element 215b, with the v-shaped elements 215a and 215b joined together at the joints 214. In an exemplary embodiment, the v-shaped elements 215a and 215b are formed such that the arms of the v-shaped elements 215a and 215b are roughly sinusoidal in shape due to the construction of the stent 200 with a laser-cutting and expansion process. In other embodiments, the v-shaped elements 215a and 215b are formed such that the arms of the v-shaped elements 215a and 215b are otherwise shaped, such as straight, convex, concave, or the like.

Figure 10:
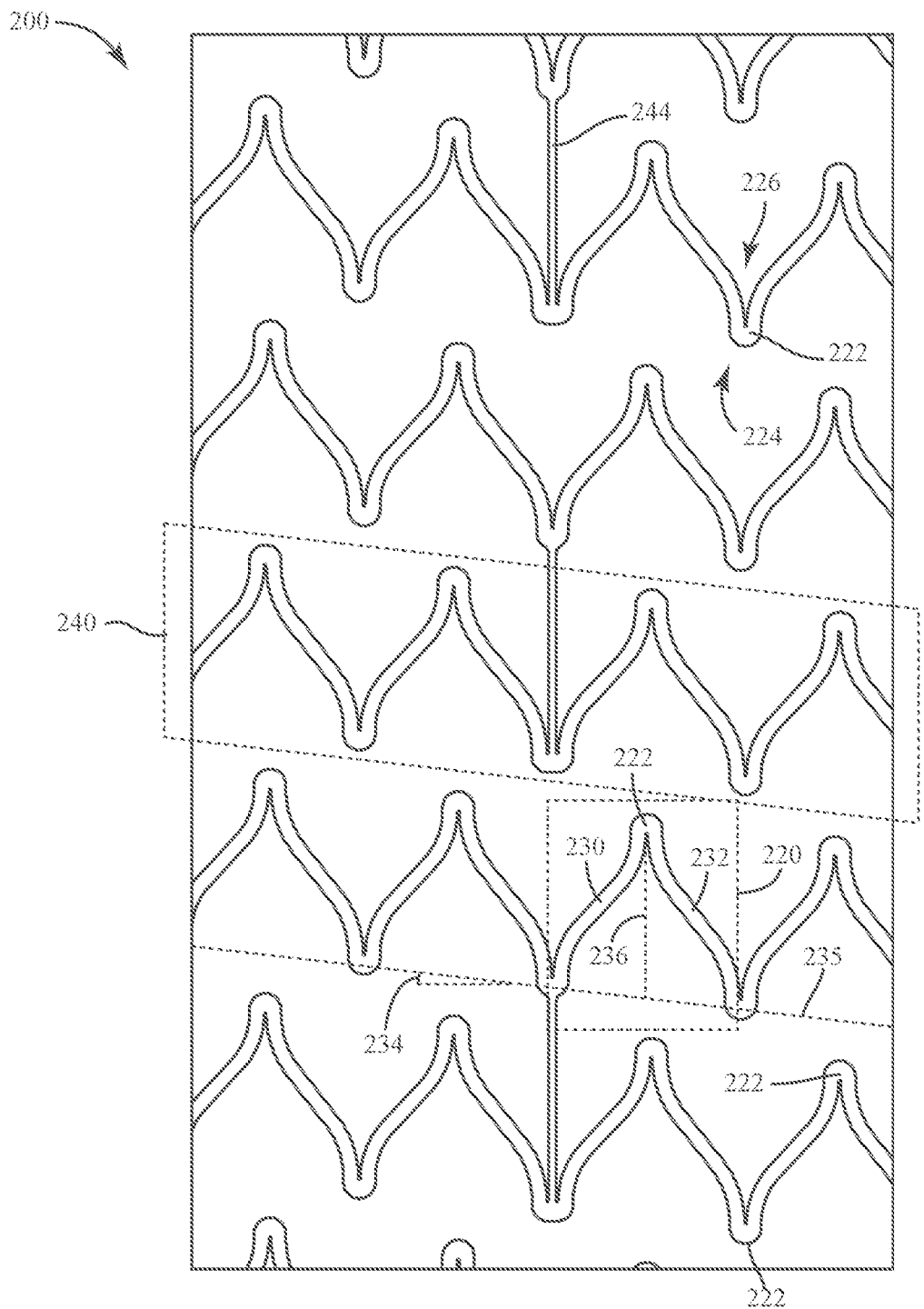
FIG. 10 is a flat view of a portion of the endoluminal prosthesis of FIG. 9.

The main body 206 of the stent 200 includes helical rings formed from v-shaped elements 220, shown in more detail in FIG. 10. With reference to FIGS. 9 and 10, the v-shaped elements 220 are sized such that the v-shaped elements 220 of each ring 240 of the helix are aligned with corresponding v-shaped elements 220 in adjacent rings 240 in a direction parallel to a longitudinal axis of the stent 200. Each of the v-shaped elements 220 is coupled to v-shaped elements 220 on either side via a joint, forming an apex 222. The v-shape of each of the v-shaped elements 220 also forms an apex 222 at the middle portion of the v-shape. A first, exterior side of each apex 222 defines a peak 224 and a second, interior side of the apex 222 defines a valley 226. Each of the v-shaped elements 220 includes a first leg 230 and a second leg 232 joined at a corresponding apex 222. The length of the second leg 232 is greater than the length of the first leg 230, forming a skewed v-shape and defining a lead angle 234 of the helical ring forming the main body 206. The lead angle 234 is shown as the angle from horizontal formed by a lead line 235 passing through the bases of the legs 230 and 232. Because the legs 230 and 232 of the v-shaped element 220 are of unequal lengths, the v-shaped element 220 is not oriented perpendicular to the lead line 235. That is, a midline 236 of the v-shaped element 220 is not perpendicular to the lead line 235. The midline 236 is defined as a line passing through the apex 222 at which the first leg 230 and second leg 232 meet and, according to an exemplary embodiment, the midline 236 of the v-shaped element 220 is oriented parallel to the longitudinal axis of the stent 200. In this way, v-shaped elements 220 that line up with each other on neighboring rings 240 form a corresponding group 242 that is parallel to the longitudinal axis of the stent 200. The skewed configuration of the v-shaped elements 220 forming the main body 206 that allow for groups 242 being oriented parallel to the longitudinal axis of the stent 200 allows the stent 200 to expand uniformly without rotating. Rotation of the rings 240 relative to each other can cause undesirable migration of the stent 200. The ring 240 is shown to be inclined at an angle equal to the lead angle 234. The lead angle 234 of the ring 240 is determined based on the desired application. In various embodiments, the lead angle 234 of each ring 240 may be increased or decreased. In some embodiments, the lead angle 234 of each ring 240 is set such that the main body 206 forms a single helix. As described in more detail below, in some embodiments, the lead angle 234 is set such that a sufficient clearance is provided between rings 240 of the helix to receive one or more additional helices, such as for a main body that may comprise a double helix, triple helix, or the like.

The v-shaped elements 220 of neighboring loops or rings 240 of the main body 206 are connected to each other with connecting struts 244 that extend from a corresponding peak 224 of one ring 240 of the helix to a corresponding valley 226 of another ring 240 of the helix. The connecting struts 244 maintain the shape of the main boy 206 of the stent 200 with the peaks 224 of one ring 240 aligned with the valleys 226 of the neighboring ring 240, and vice-versa, thereby increasing the flexibility of the main body 206 and reducing the likelihood that a ring will impede an adjacent ring. Each ring 240 may be connected via connecting struts 244 extending from valleys 226 to peaks 224 of one adjacent ring 240 and may be connected via connecting struts 244 extending from peaks 224 to valleys 226 of another adjacent ring 240. Accordingly, one side of the ring 240 has valleys 226 that are coupled to connecting struts 244 and another side of the ring 240 has peaks 224 that are coupled to connecting struts 244.

Each apex 222 of the v-shaped elements 220 forming the main body 206 may initiate and receive connecting struts 244 that connect to corresponding apices 222 of the v-shaped elements 220 of the adjacent ring 240. The connecting struts 244 may be coupled to any apex 222 of the main body 206, such as a corresponding apex 222 formed between the legs 230 and 232 of a v-shaped element 220 or the apex 222 formed between adjacent v-shaped elements 220. In various embodiments, the frequency of connecting struts 244 and the ratio of apices 222 joined by connecting struts 244 versus free apices 222 may vary. In some embodiments, a distance between each of the connecting struts 244 is greater than a width of one of the v-shaped elements 220. In some embodiments, a distance between each of the connecting struts 244 is greater than double a width of one of the v-shaped elements 220. In some embodiments, as shown in FIG. 9, the connecting struts 244 are spaced from each other such that four v-shaped elements 220 in each ring 240 are provided between each connecting strut 244 that is on one side of the ring 240.

The main body 206 may be subdivided into a series of sub-rings 246 including four v-shaped elements 220, each of which are coupled to an adjacent sub-ring 246 on one side with a connecting strut 244 from a corresponding valley 226 to a corresponding peak 224 and coupled to an adjacent sub-ring 246 on the opposite side with a connecting strut 244 from a corresponding peak 224 to a corresponding valley 226. In some embodiments, the number of connecting struts 244 between adjacent rings 240 may vary. For example, some rings 240 may be coupled together with three connecting struts 244, while other rings 240 may be connected together with two connecting struts 244. Increasing the number of connecting struts 244 between rings 240 may decrease the flexibility of the stent 200 and conversely decreasing the number of connecting struts 244 between rings 240 may increase the flexibility of the stent 200. In various embodiments, a particular connecting strut of the connecting struts 244 that is on one side of a particular ring of the rings 240 is equidistant from a corresponding two connecting struts of the connecting struts 244 that are nearest to the particular connecting strut.

Referring still to FIG. 9, the first transition region 204 and the second transition region 208 transition from the end rings 202 and 210, respectively, to the helical main body 206. In various embodiments, the rings 240 are angled with respect to the end rings 202 and 210. In various embodiments, a width direction of an end of the first end ring 202 and a width direction of an end of the second end ring 210 are perpendicular to the longitudinal axis of the stent 200. The first transition region 204 couples the first end ring 202 to the main body 206 and, on the other end of the stent 200, the second transition region 208 connects the second ring 210 to the main body 206. The transition regions 204 and 208 may include one or more bridges or struts 248a, 248b, and 248c that connect one or more of the apices 216 of the end rings 202 and 210, respectively, to the corresponding apices 222 of an adjacent helical ring 240 of the main body 206. In various embodiments, the connecting struts 244 coupling together adjacent rings 240 of the main body 260 are configured to connect a corresponding peak 224 of one ring 240 to a corresponding valley 226 of another ring 240 to allow for flexibility of the main body 206. In various embodiments, the struts 248a, 248b, and 248c of the transition regions 204 and 208 that connect the end rings 202 and 210, respectively, to the main body 206 form a peak-to-peak connection between the apices 216 and the apices 222 to increase the stiffness of the end portions 202 and 210.

Because the rings 240 of the helical main body 206 are angled relative to the end rings 202 and 210 that have straight ends, the distance between the main body 206 and the end rings 202 and 210 that is spanned by the struts 248a, 248b, and 248c varies about the circumference of the stent 200. Accordingly, the lengths of the struts 248a, 248b, and 248c that connect the end rings 202 and 210 vary from one another. In some embodiments, the helically shaped main body 206 may be coupled directly to one of the apices 216 of the end rings 202 and 210. In some embodiments, the first transition region 204 includes a direct connection 218 between a corresponding apex 216 of the end ring 202 and the corresponding apex 222 of the main body 206, such as a strut with minimal or zero length, and also includes the first strut 248a, the second strut 248b with a length greater than the first strut 248a, and the third strut 248c with a length greater than the length of the second strut 248b. According to an exemplary embodiment, the third strut 248c has a length approximately equal to the height of a v-shaped element 220 of the main body 260. It is to be understood that the second transition region 208 may be similar in construction to the first transition region 204 as in FIG. 9, or may vary in construction compared to the first transition region 204. For example, in some embodiments, the second transition region 208 may include more or fewer struts as compared to the first transition region 204 for connecting to the main body 206.

In some embodiments, the transition regions 204 and 208 may include bridges, such as the struts 248a, 248b, and 248c, that are variably spaced apart from each other. In some embodiments, the distance between direct connection 218 and the first strut 248a is equal to the width of two v-shaped elements 220, the distance between the first strut 248a and the second strut 248b is equal to the width of three v-shaped elements 220, and the distance between the second strut 248b and the third strut 248c is equal to the width of four v-shaped elements 220. In other embodiments, the struts 248a, 248b, and 248c may be otherwise spaced.

Figure 11:
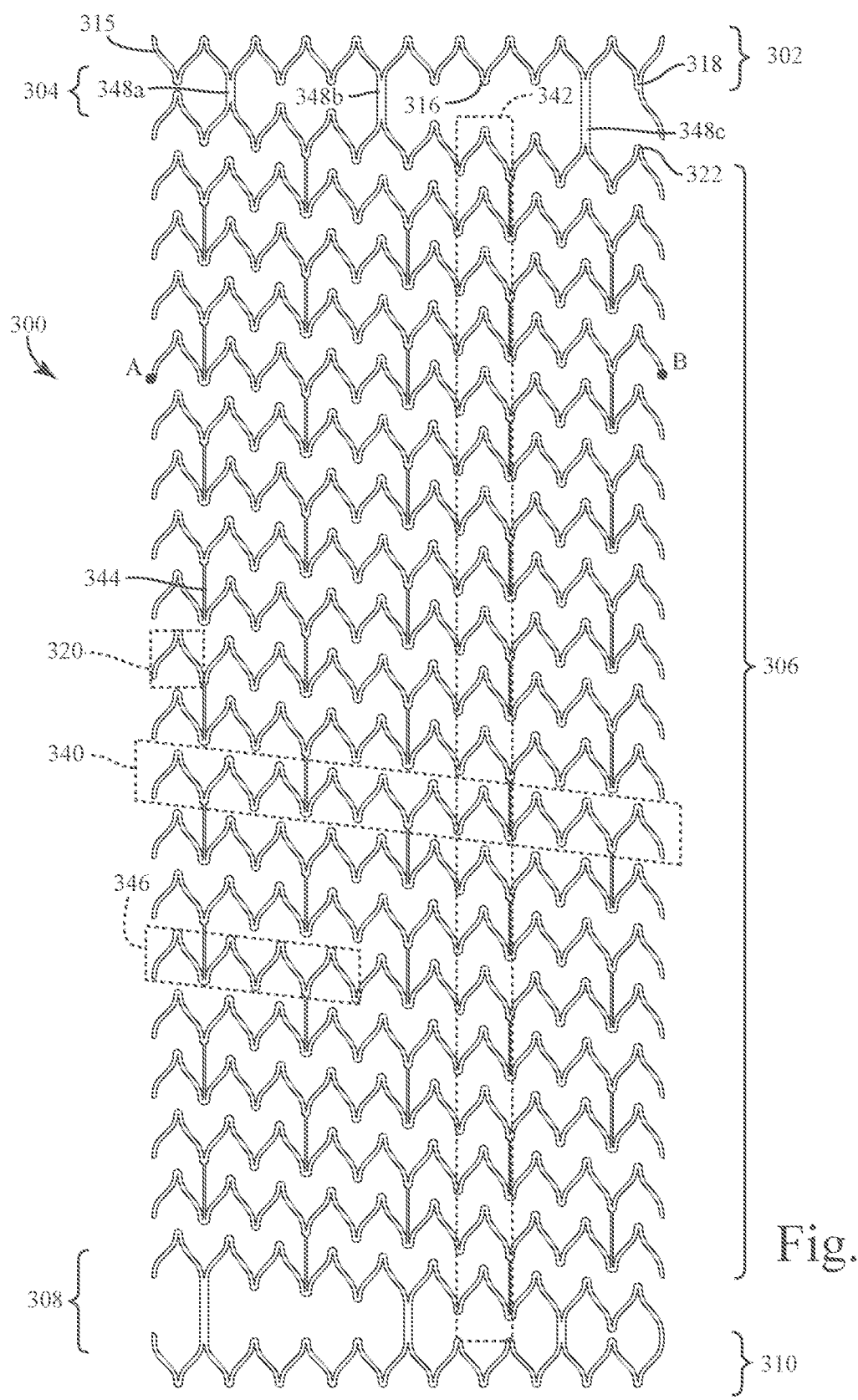
FIG. 11 is a flat view of an endoluminal prosthesis, according to another exemplary embodiment.

Referring to FIGS. 11, 12, 13, 14, and 15, a stent 300 is shown according to another exemplary embodiment. The stent 300 may be similar in shape to the stents 100 (refer to FIG. 1) and 200 (refer to FIG. 9), discussed above. The stent 300 includes a first end ring 302, a first transition region 304, a main body 306, a second transition region 308, and a second end ring 310. While the stent 300 is generally manufactured to be a generally cylindrical body, the flat view illustrated in FIG. 11 is provided for clarity. End points on one side of the stent 300, as shown by point A are understood to be continuous with corresponding end points on the opposite side of the stent 300, as shown by point B.

With reference to FIGS. 11, 12, 13, 14, and 15, the end rings 302 and 310 are shown to be formed from v-shaped elements 315 that form apices 316. In other embodiments, the end rings 302 and 310 may include otherwise shaped elements, such as the diamond shaped or tear drop shaped elements described above.

The transition regions 304 and 308 couple the main body 306 to the end rings 302 and 310, respectively. The transition regions 304 and 308 include one or more bridges or struts 348a, 348b, and 348c, that connect one or more of the apices 316 of the end rings 302 or 310 to the corresponding apices 322 of an adjacent helical ring 340 of the main body 306 with a peak-to-peak connection. The first transition region 304 includes a direct connection 318 between a corresponding apex 316 of the end ring 302 and the corresponding apex 322 of the main body 306, such as a strut with minimal or zero length. The first transition region 304 also includes the first strut 348a, the second strut 348b with a length greater than the length of the first strut 348a, and a third strut 348c with a length greater than the length of the second strut 348b. According to an exemplary embodiment, the third strut 348c has a length approximately equal to the height of a v-shaped element 320 of the main body 306. It is to be understood that the second transition region 308 may be similar in construction to the first transition region 304 or may vary in construction compared to the first transition region 304. For example, the transition region 308 may include more or fewer struts as compared to the first transition region 304.

The main body 306 includes the helical rings 340 formed from skewed, v-shaped elements 320 that each have two legs with one leg longer than the other leg. The legs of the v-shaped elements 320 are sized such that the v-shaped elements 320 of each ring 340 of the helix are aligned with other corresponding v-shaped elements 320 in the adjacent rings 340 in a direction parallel to a longitudinal axis of the stent 300. Each of the v-shaped elements 320 is coupled to v-shaped elements 320 on either side within a corresponding ring 340 via a joint, forming a corresponding apex 322. The v-shaped elements 320 on neighboring rings 340 of the helical main body 306 form groups 342 that are parallel to the longitudinal axis of the stent 300. In some embodiments, the v-shaped elements 320 of neighboring rings 340 of the main body 306 are connected to each other with connecting struts 344. The main body 306 may be subdivided into a series of repeating sub-rings 346 that each include four v-shaped elements 320, and each of which are coupled to an adjacent sub-ring 346 on one side with a connecting strut 344 extending from a corresponding peak and coupled to an adjacent sub-ring 346 on the opposite side with a connecting strut 344 extending from a corresponding valley.

Referring to FIGS. 9 and 11, the stent 200 is generally constructed similarly to the stent 300, with the main body 306 of the stent 300 having additional rings 340 as compared to the number of rings 240 of the main body 206 of the stent 200, thereby providing an increased length of the stent 300 as compared to the stent 200. A longer stent can be more flexible than a shorter stent and may be advantageously deployed in a vessel having a larger aneurysm. In various embodiments, the stent 300 may be tapered from one end to another end in the longitudinal direction.

Referring to FIGS. 16, 17, 18, 19, and 20, a stent 350 is shown according to another exemplary embodiment. The stent 350 includes the first end ring 302, the main body 306, and the second end ring 310 that are similar in construction to the stent 300 (refer to FIG. 11).

The transition regions 354 and 358 of the stent 350 couple the main body 306 to the end rings 302 and 310, respectively. In contrast to the stent 300 (refer to FIG. 11), which includes struts 348a, 348b, and 348c coupling only some of the apices 316 of the end rings 302 or 310 to the apices 322 of the main body 306, the stent 350 include struts 360 of various lengths connecting each of the apices 316 of the end rings 302 or 310 to the corresponding apex 322 of an adjacent ring 340 of the main body 306 with a peak-to-peak connection. By providing struts 360 connecting each of the apices 316 of the end rings 302 or 310 to the apices 322 of the adjacent ring 340 of the main body 306, the stent 350 provides an end portion that is substantially stiffer than the end portion of the stent 300 (refer to FIG. 11).

Figure 21:
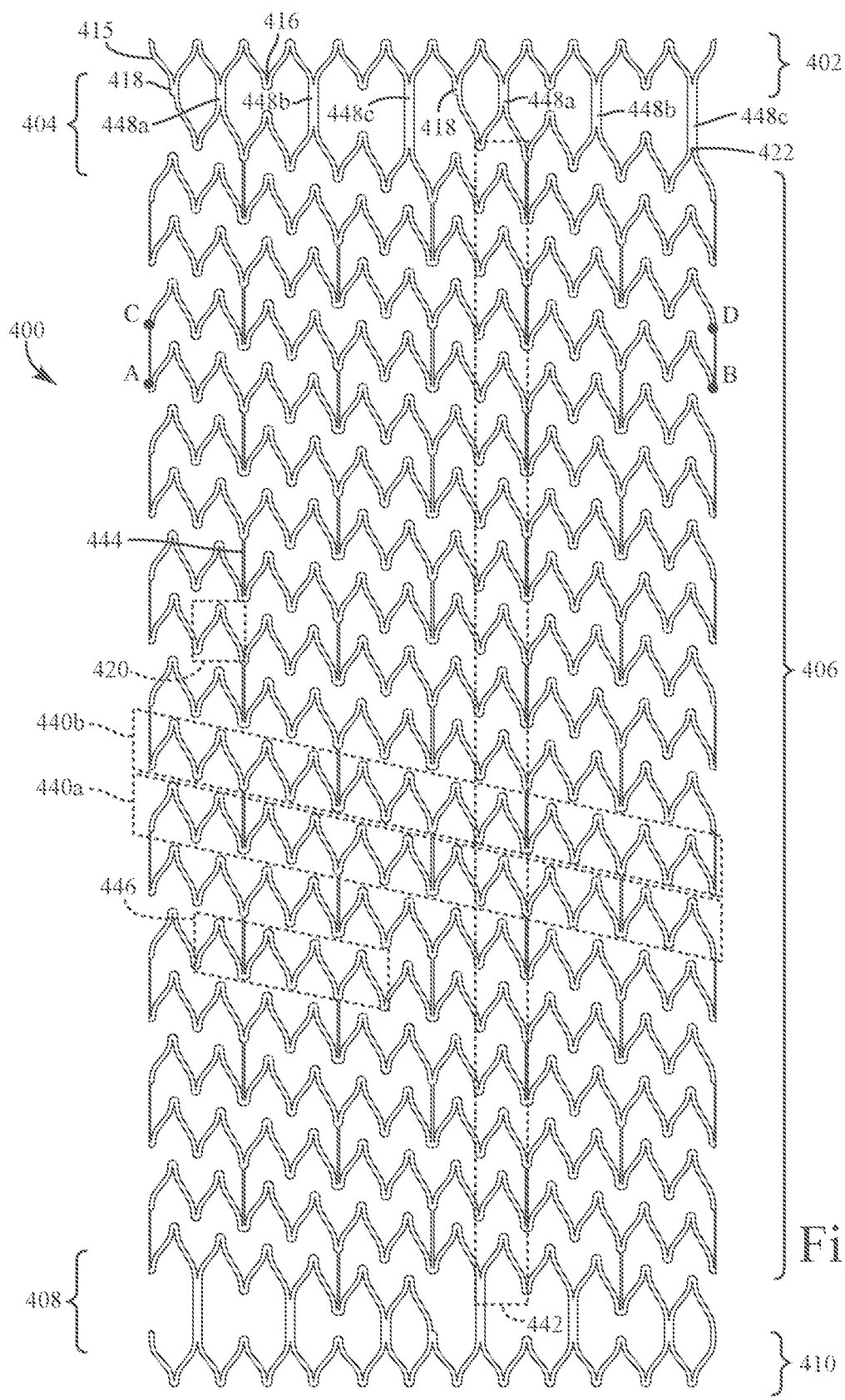
FIG. 21 is a flat view of an endoluminal prosthesis, according to another exemplary embodiment.

Referring to FIGS. 21, 22, 23, 24, and 25, a stent 400 is shown according to another exemplary embodiment. The stent 400 includes a first end ring 402, a first transition region 404, a main body 406, a second transition region 408, and a second end ring 410. While the stent 400 is generally manufactured to be a generally cylindrical body, the flat view illustrated in FIG. 21 is provided for clarity. End points on one side of the stent 400, as shown by points A and C are understood to be continuous with corresponding end points on the opposite side of the stent 400, as shown by points B and D, respectively.

The end rings 402 and 410 are shown to be formed from v-shaped elements 415 that form apices 416. In other embodiments, the end rings 402 and 410 may include otherwise shaped elements, such as the diamond shaped or tear drop shaped elements described above.

In contrast to the stents 100, 200, 300, and 350 described above (refer to FIGS. 1, 9, 11, and 16), the main body 406 includes alternating helical rings 440a, 440b formed from skewed, v-shaped elements 420, where the alternating helical rings 440a, 440b are connected differently at ends than the rings in the stents 100, 200, 300, and 350. The main body 406 includes the helical rings 440a, 440b formed from skewed, v-shaped elements 420 that each have two legs with one leg longer than the other leg. The legs of the v-shaped elements 420 are sized such that the v-shaped elements 420 of each ring 440a, 440b of the helix are aligned with other corresponding v-shaped elements 420 in the adjacent rings 440a, 440b in a direction parallel to a longitudinal axis of the stent 400. Each of the v-shaped elements 420 is coupled to v-shaped elements 420 on either side via a joint, forming an apex 422.

According to an exemplary embodiment, the main body 406 includes the helical rings 440a, 440b forming a double helix. The helices are intertwined, with rings 440a of the first helix alternating with rings 440b of the second helix of the main body 406. The v-shaped elements 420 on neighboring rings 440a and 440b form groups 442 in a direction that is parallel to the longitudinal axis of the stent 400. In some embodiments, the v-shaped elements 420 of neighboring rings 440a and 440b of the main body 406 are connected to each other with connecting struts 444. The main body 406 may be subdivided into a series of sub-rings 446 including four v-shaped elements 420, each of which are coupled to an adjacent sub-ring 446 on one side with a connecting strut 444 extending from a peak and coupled to an adjacent sub-ring 446 on the opposite side with a connecting strut 444 extending from a valley. In various embodiments, each of the corresponding rings 440a and 440b may be coupled together with three connecting struts 444 between each ring 440a and 440b. In various embodiments, an even distribution of connecting struts 444 between the rings 440a and 440b improves pressure distribution along the length of the main body 406, such as for providing a pressure applied by the main body 406 to the walls of a blood vessel in which the stent 400 is disposed, and improves the long-term durability of the stent 400. In various embodiments, the number and distribution of the connecting struts 444 may vary. Increasing the number of connections may decrease the flexibility of the endoluminal prosthesis, and conversely decreasing the number of connections may increase the flexibility of the endoluminal prosthesis.

The transition regions 404 and 408 couple the main body 406 to the end rings 402 and 410, respectively. The transition regions 404 and 408 include one or more bridges or struts 448a, 448b, and 448c that connect one or more of the apices 416 of the end rings 402 or 410 to the corresponding apices 422 of an adjacent helical ring of the main body 406 with a peak-to-peak connection. For each of the helical rings, such as the rings 440a or 440b that are proximate to the end ring 402, the first transition region 404 includes a direct connection 418 between an apex 416 of the end ring 402 and a corresponding apex 422 of the main body 406, such as a strut with minimal or zero length, and the first transition region 404 also includes first struts 448a, second struts 448b with a length greater than the length of the first struts 448a, and third struts 448c with a length greater than the length of the second struts 448b. According to an exemplary embodiment, the third struts 448c each have a length approximately equal to the height of the v-shaped elements 420 of the main body 406. It is to be understood that the second transition region 408 may be similar in construction to the first transition region 404 or may vary in construction compared to the first transition region 404. For example, the second transition region 408 may include more or fewer struts as compared to the first transition region 404.

Referring to FIGS. 26, 27, 28, 29, and 30, a stent 450 is shown according to another exemplary embodiment. The stent 450 includes the first end ring 402, the main body 406, and the second end ring 410 that are similar in construction to the stent 400 (refer to FIG. 21), and like numbered labels represent similar elements among the figures.

The transition regions 454 and 458 couple the main body 406 to the end rings 402 and 410, respectively. In contrast to the stent 400 (refer to FIG. 21), which includes struts 448a, 448b, and 448c coupling only some of the apices 416 of the end rings 402 or 410 to the apices 422 of the main body 406, the stent 450 include struts 460 of various lengths connecting each of the apices 416 of the end rings 402 or 410 to the corresponding apices 422 of adjacent helical rings of the main body 406 with peak-to-peak connections. By providing struts 460 connecting each of the apices 416 of the end rings 402 or 410 to the corresponding apices 422 of the adjacent helical rings of the main body 406, the stent 450 provides an end portion that is substantially stiffer than the end portion of the stent 400 (refer to FIG. 21).

Figure 12:
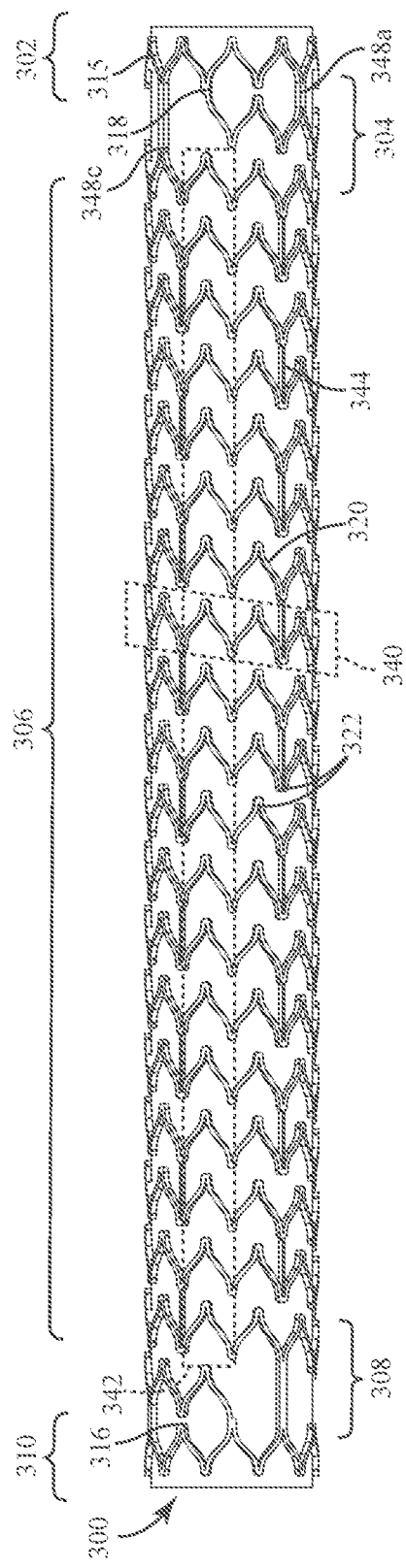
FIG. 12 is a front orthogonal view of the endoluminal prosthesis of FIG. 11.
Figure 13:
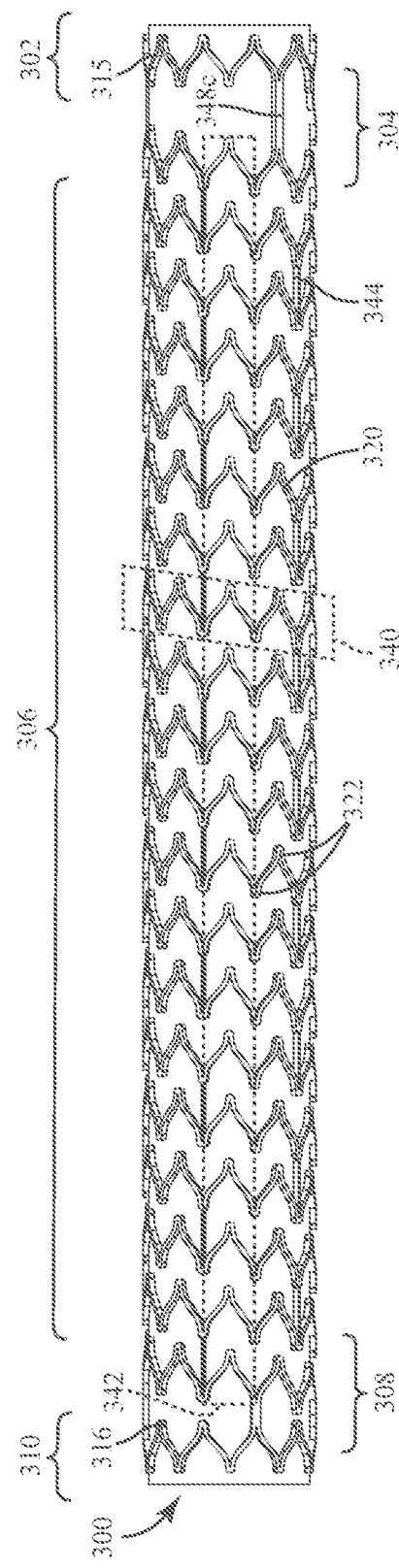
FIG. 13 is a top orthogonal view of the endoluminal prosthesis of FIG. 11.
Figure 14:
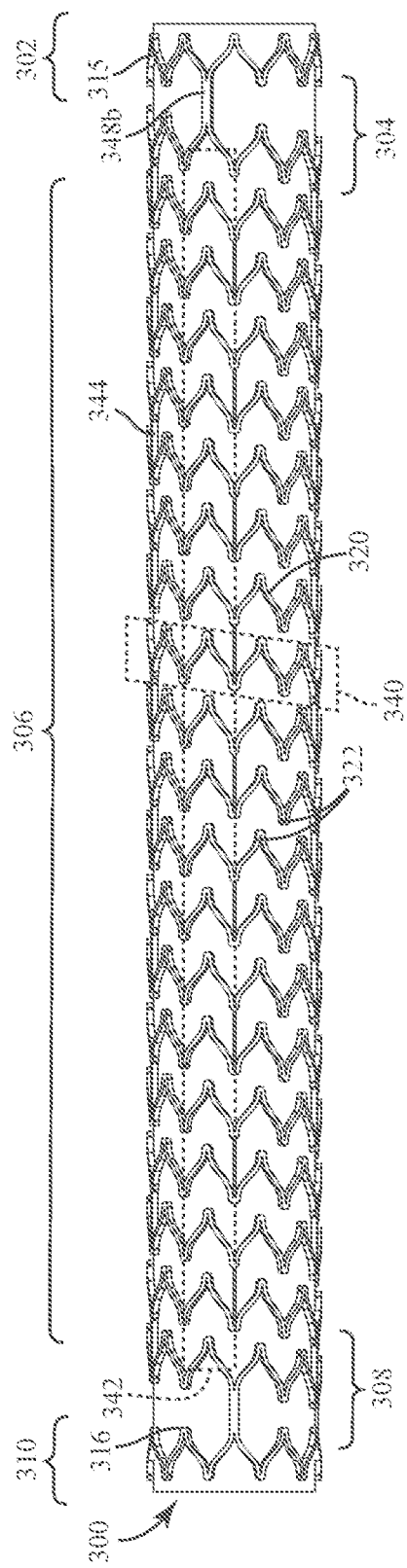
FIG. 14 is a rear orthogonal view of the endoluminal prosthesis of FIG. 11.
Figure 15:
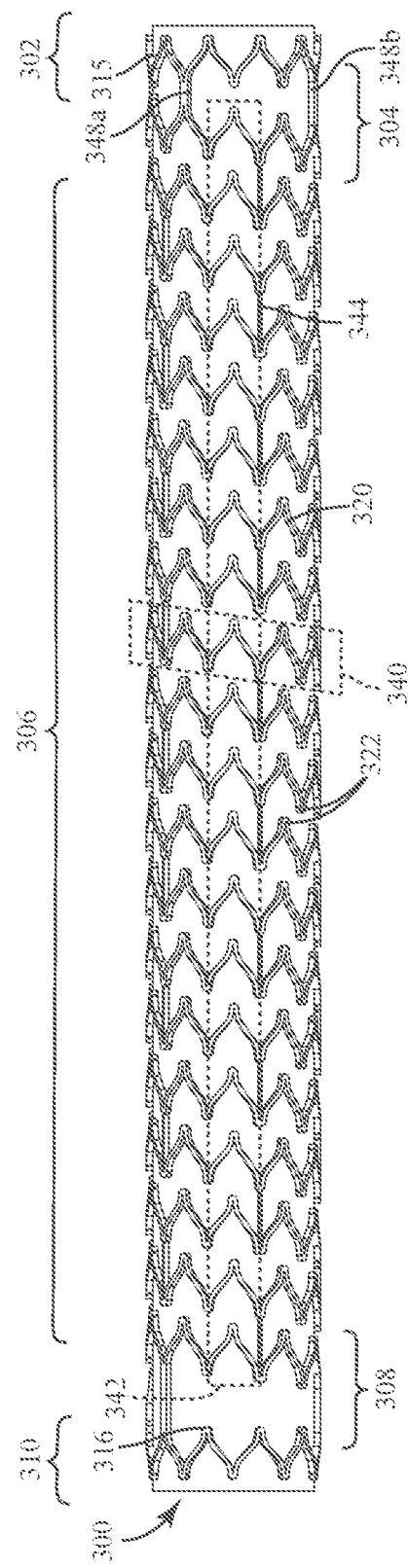
FIG. 15 is a bottom orthogonal view of the endoluminal prosthesis of FIG. 11.
Figure 16:
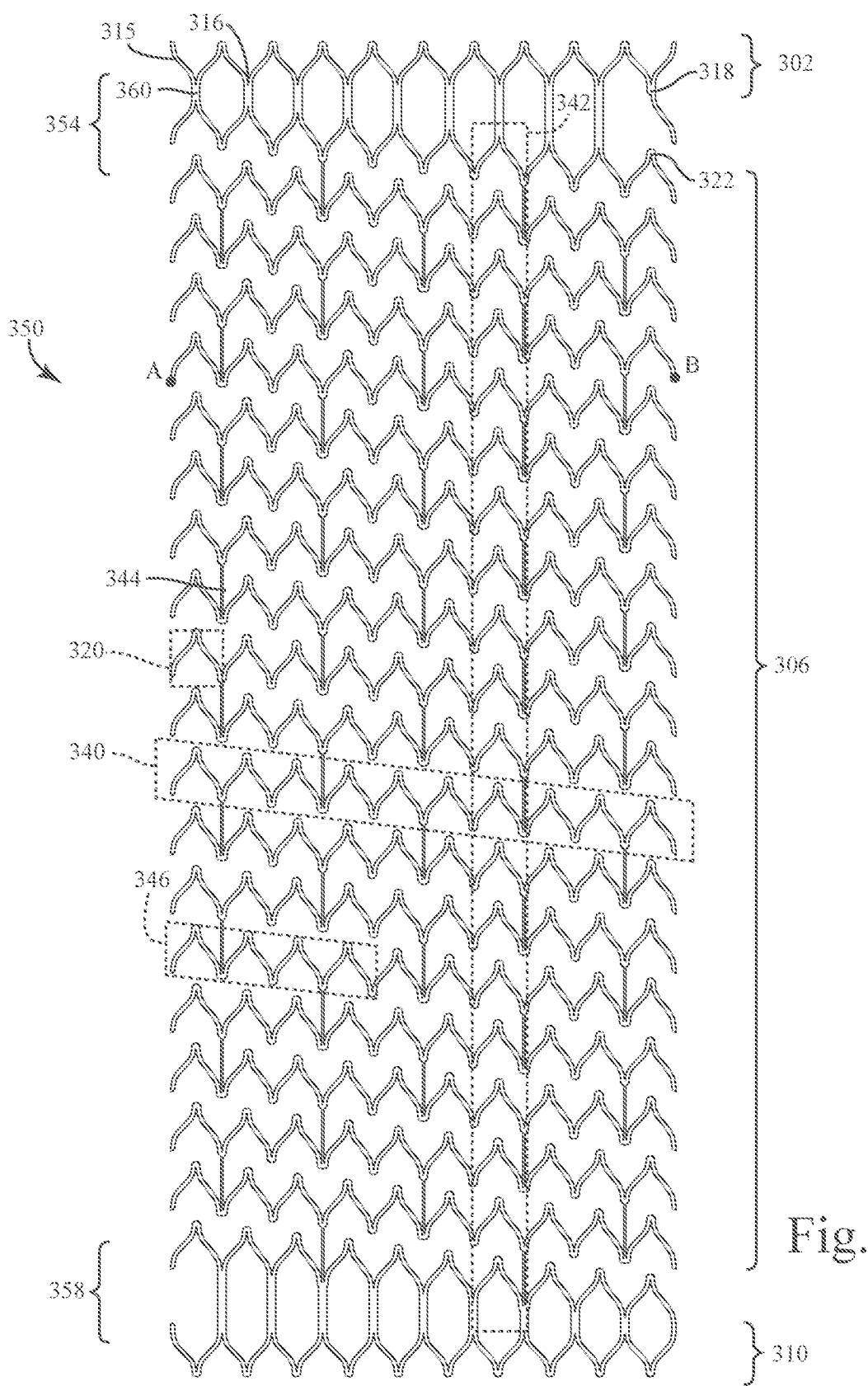
FIG. 16 is a flat view of an endoluminal prosthesis, according to another exemplary embodiment.
Figure 17:
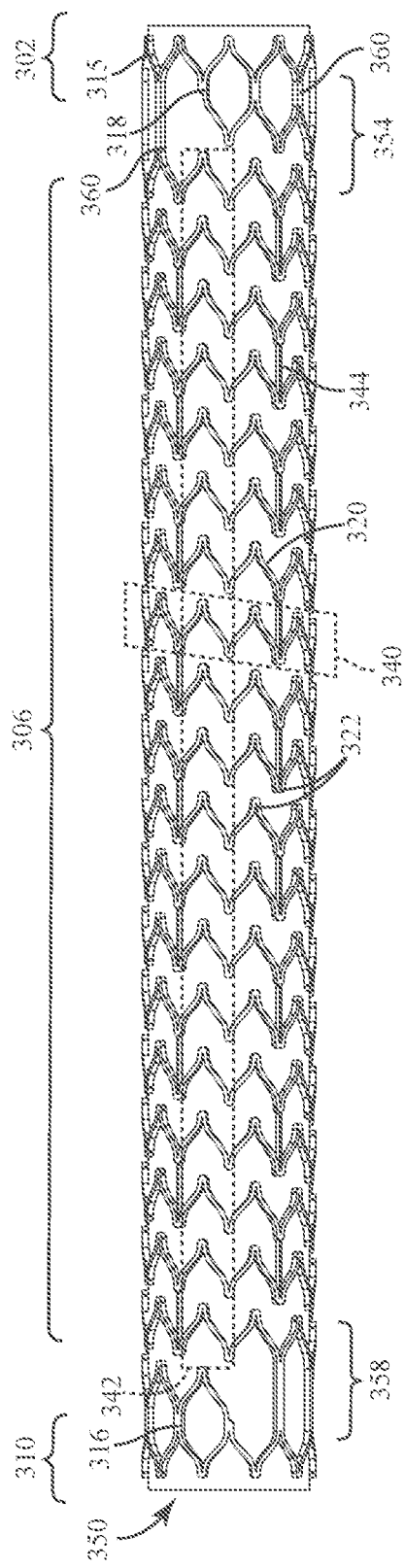
FIG. 17 is a front orthogonal view of the endoluminal prosthesis of FIG. 16.
Figure 18:
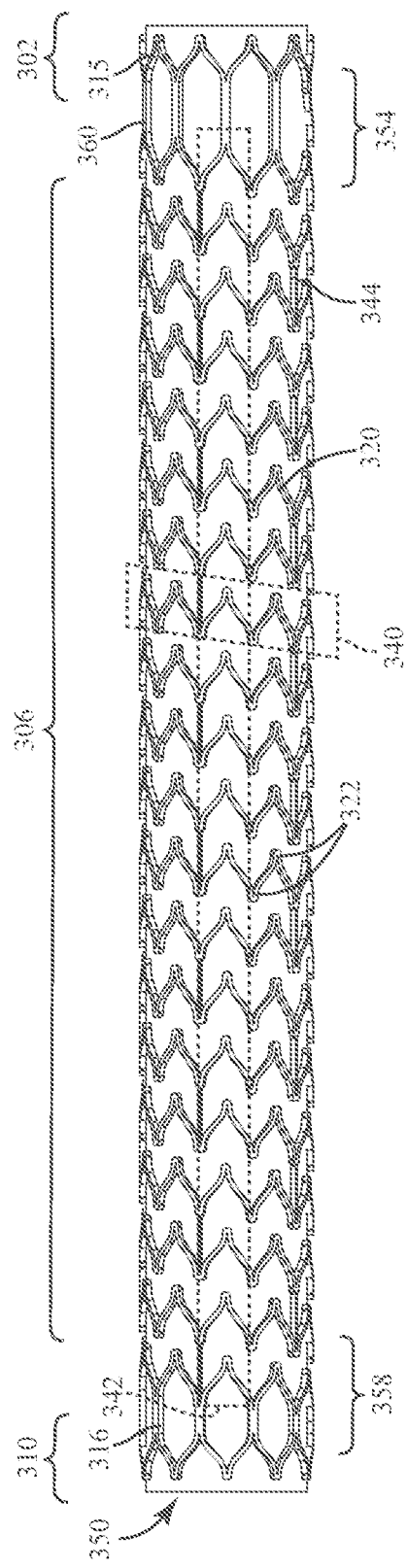
FIG. 18 is a top orthogonal view of the endoluminal prosthesis of FIG. 16.

With reference to FIG. 1, a method of manufacturing in accordance with an embodiment includes manufacturing the stent 100 having the structure depicted in FIG. 1. Also, a method of use of the stent 100 in accordance with an embodiment includes inserting the stent 100 into a blood vessel of a patient in an unexpanded state, and then expanding the stent 100 within the blood vessel. With reference to FIG. 9, a method of manufacturing in accordance with an embodiment includes manufacturing the stent 200 having the structure depicted in FIG. 9. Also, a method of use of the stent 200 in accordance with an embodiment includes inserting the stent 200 into a blood vessel of a patient in an unexpanded state, and then expanding the stent 200 within the blood vessel. With reference to FIGS. 11 and 12, a method of manufacturing in accordance with an embodiment includes manufacturing the stent 300 having the structure depicted in FIGS. 11 and 12. Also, a method of use of the stent 300 in accordance with an embodiment includes inserting the stent 300 into a blood vessel of a patient in an unexpanded state, and then expanding the stent 300 within the blood vessel. With reference to FIGS. 16 and 17, a method of manufacturing in accordance with an embodiment includes manufacturing the stent 350 having the structure depicted in FIGS. 16 and 17. Also, a method of use of the stent 350 in accordance with an embodiment includes inserting the stent 350 into a blood vessel of a patient in an unexpanded state, and then expanding the stent 350 within the blood vessel.

Figure 22:
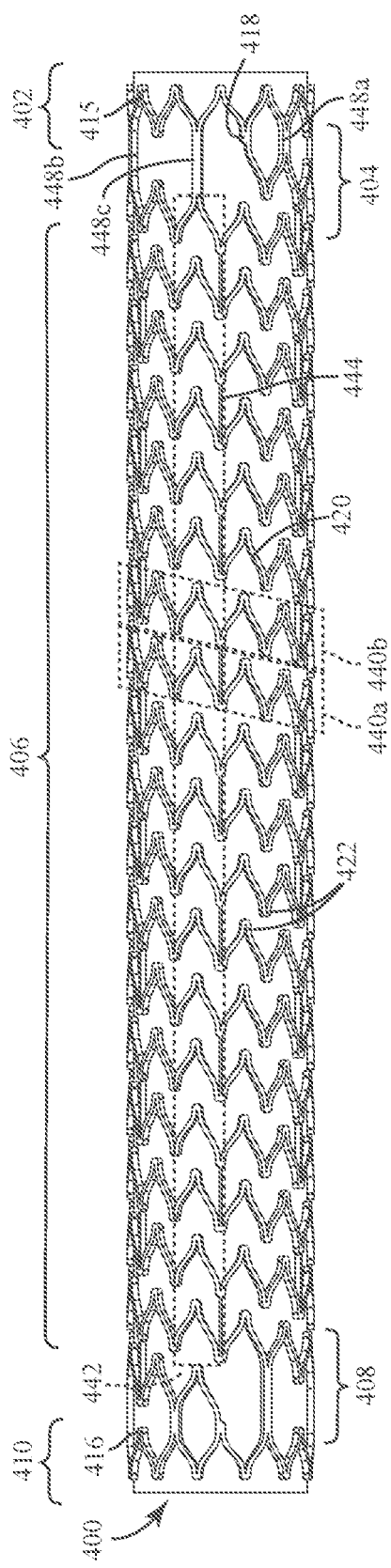
FIG. 22 is a front orthogonal view of the endoluminal prosthesis of FIG. 21.
Figure 23:
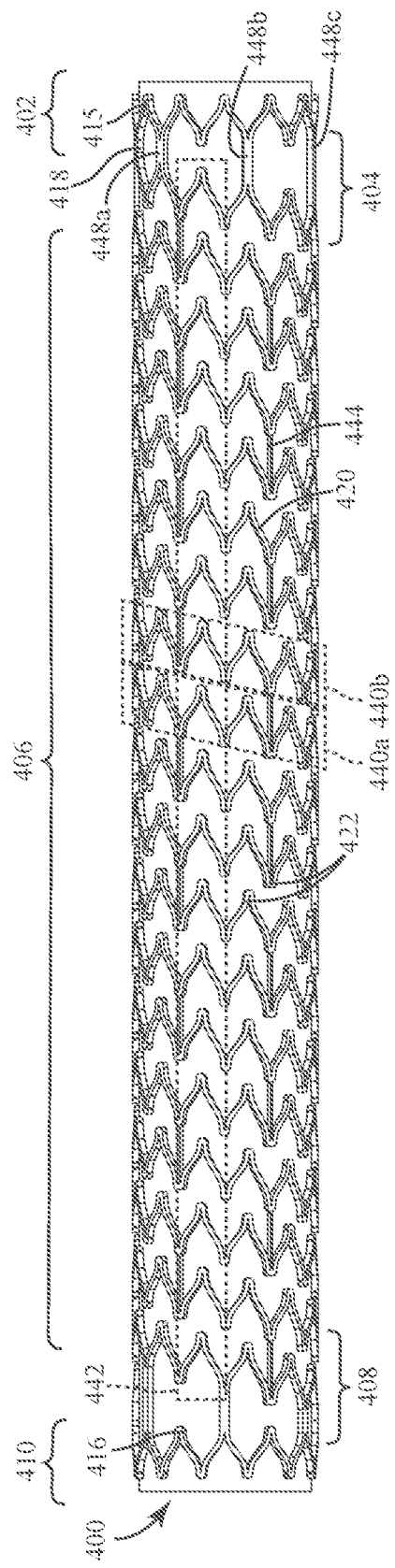
FIG. 23 is a top orthogonal view of the endoluminal prosthesis of FIG. 21.
Figure 26:
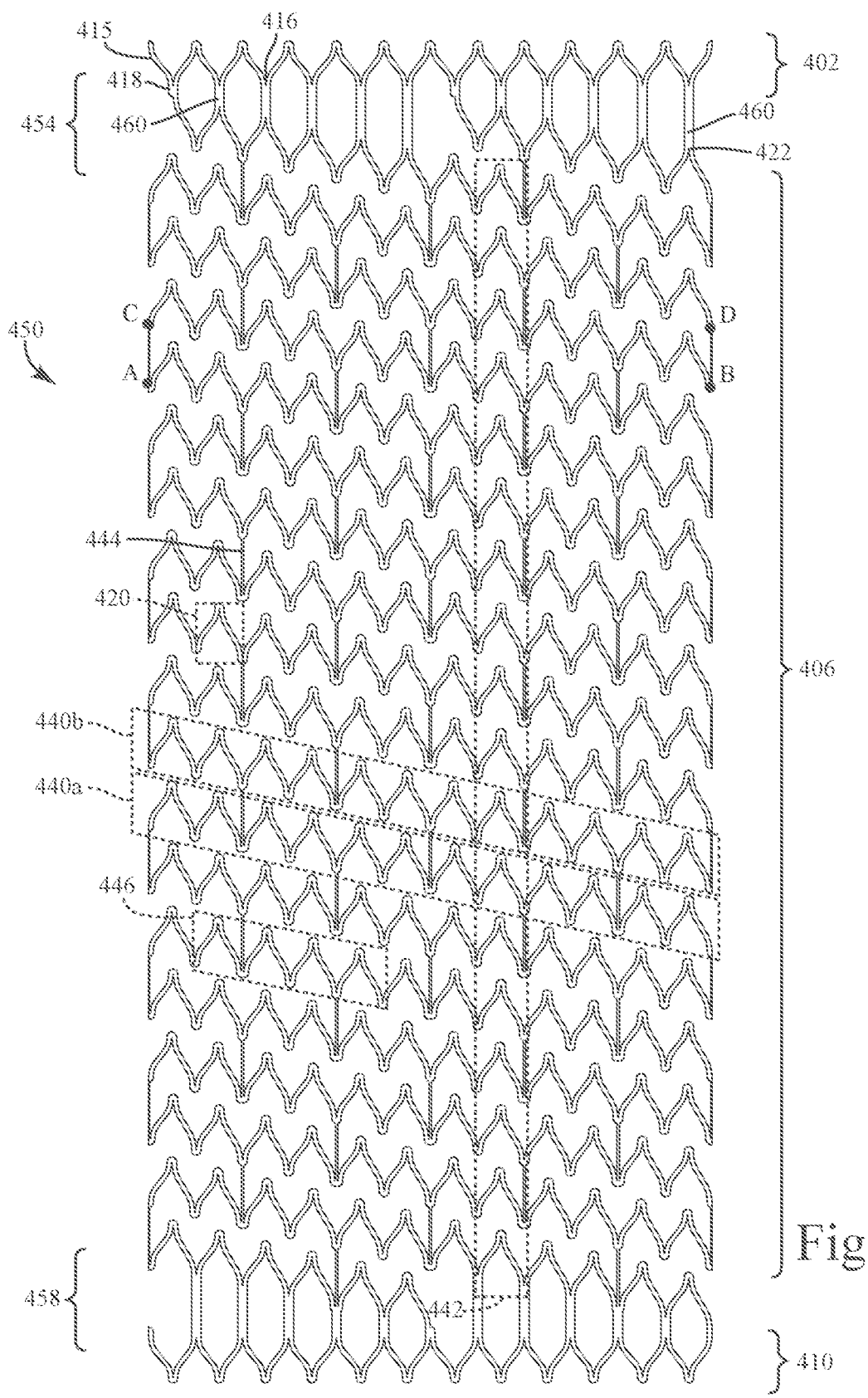
FIG. 26 is a flat view of an endoluminal prosthesis, according to another exemplary embodiment.
Figure 29:
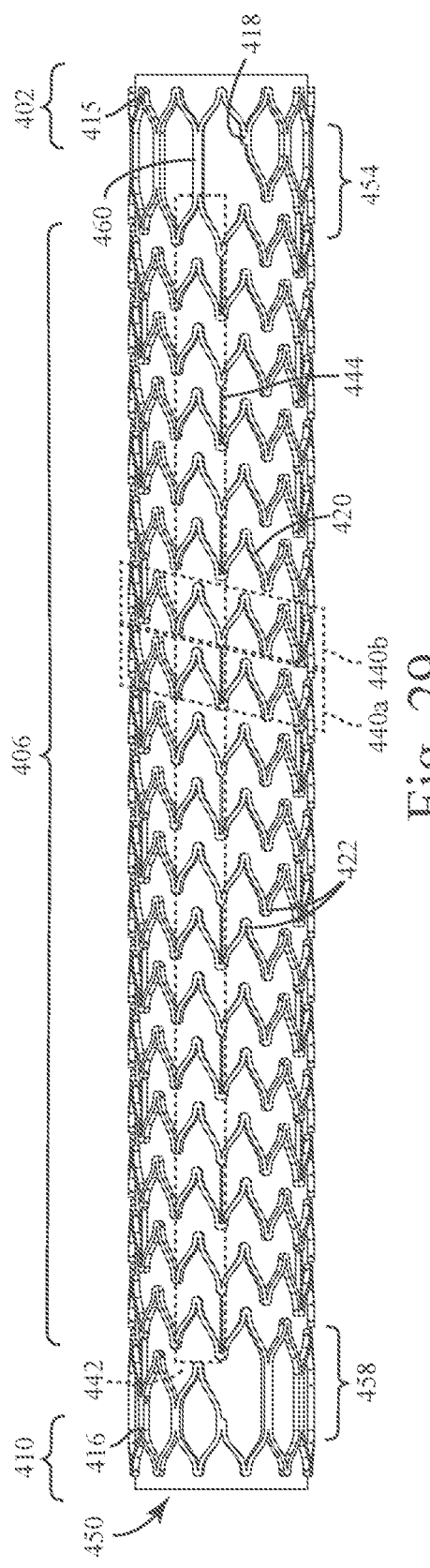
FIG. 29 is a rear orthogonal view of the endoluminal prosthesis of FIG. 26.
Figure 30:
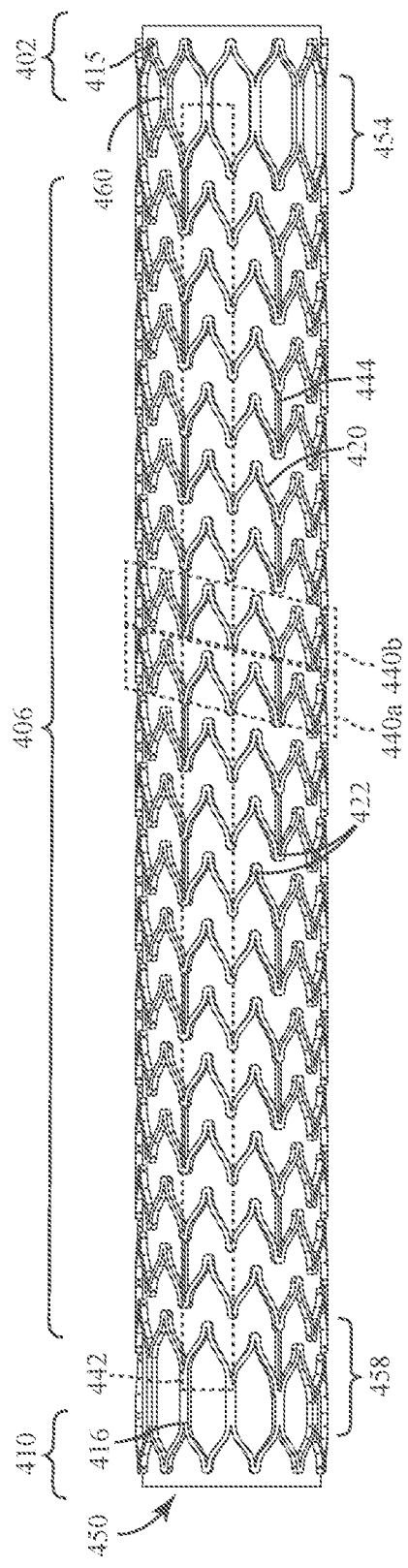
FIG. 30 is a bottom orthogonal view of the endoluminal prosthesis of FIG. 26.

With reference to FIGS. 21 and 22, a method of manufacturing in accordance with an embodiment includes manufacturing the stent 400 having the structure depicted in FIGS. 21 and 22. Also, a method of use of the stent 400 in accordance with an embodiment includes inserting the stent 400 into a blood vessel of a patient in an unexpanded state, and then expanding the stent 400 within the blood vessel. With reference to FIGS. 26 and 27, a method of manufacturing in accordance with an embodiment includes manufacturing the stent 450 having the structure depicted in FIGS. 26 and 27. Also, a method of use of the stent 450 in accordance with an embodiment includes inserting the stent 450 into a blood vessel of a patient in an unexpanded state, and then expanding the stent 450 within the blood vessel.

Various embodiments described above may eliminate the need for manual working post laser cutting of a stent. The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

What is claimed is:

1. A stent, comprising:
a main body comprising a plurality of rings that form a helix, each of the plurality of rings comprising a plurality of skewed v-shaped elements that each have a first leg and a second leg that is longer than the first leg;
an end ring is shaped to have a plurality of apices of the end ring; and
a transition region;
wherein the plurality of skewed v-shaped elements of a ring of the plurality of rings form a plurality of apices of the ring;
wherein the transition region includes a connection between a corresponding apex of the plurality of apices of the end ring to a corresponding apex of the plurality of apices of the ring;
wherein the transition region includes a plurality of struts that each connect a corresponding apex of the plurality of apices of the end ring to a corresponding apex of the plurality of apices of the ring;
wherein the transition region includes a first gap and a second gap;
wherein the first gap is between a first apex of the plurality of apices of the end ring and a second apex of the plurality of apices of the ring, wherein the second apex is opposing to the first apex, a direct distance between the first apex and the second apex defines a length of the first gap;
wherein the second gap is between a third apex of the plurality of the apices of the end ring and a fourth apex of the plurality of apices of the ring,
wherein a direct distance between the third apex and the fourth apex defines a length of the second gap;
wherein the length of the first gap is different from the length of the second gap;
wherein at least one apex of the end ring is an apex of a tear drop shaped element;

wherein the tear drop shaped element includes a first v-shaped element having legs that are a same length as each other and a second v-shaped element having legs that are a same length as each other; and wherein the legs of the first v-shaped element of the tear drop shaped element are longer than the legs of the second v-shaped element of the tear drop shaped element.

2. The stent of claim 1, wherein a length of a second strut of the plurality of struts is longer than a length of a first strut of the plurality of struts.

3. The stent of claim 2, wherein a length of a third strut of the plurality of struts is longer than the length of a second strut of the plurality of struts.

4. The stent of claim 3, wherein a distance between the first strut and the second strut is equal to a width of three skewed v-shaped elements of a plurality of skewed v-shaped elements of the ring; and wherein a distance between the second strut and the third strut is equal to a width of four skewed v-shaped elements of the plurality of skewed v-shaped elements of the ring.

5. The stent of claim 1, further comprising:

a plurality of connecting struts for connecting the ring of the plurality of rings of the main body with an adjacent ring of the plurality of rings of the main body.

6. The stent of claim 5, wherein each of the plurality of connecting struts extends from a corresponding peak of a plurality of peaks of the ring to a corresponding valley of a plurality of valleys of the adjacent ring.

7. The stent of claim 5, wherein a distance between each of the plurality of connecting struts is greater than a width of a skewed v-shaped element of the plurality of skewed v-shaped elements.

8. The stent of claim 5, wherein a distance between each of the plurality of connecting struts is greater than double a width of a skewed v-shaped element of the plurality of skewed v-shaped elements.

9. The stent of claim 1, further comprising:

a first plurality of connecting struts for connecting a particular ring of the plurality of rings of the main body with a first adjacent ring of the plurality of rings of the main body; and a second plurality of connecting struts for connecting the particular ring with a second adjacent ring of the plurality of rings of the main body;

wherein each of the first plurality of connecting struts extends from a corresponding peak of a plurality of peaks of the particular ring to a corresponding valley of a plurality of valleys of the first adjacent ring; and wherein each of the second plurality of connecting struts extends from a corresponding valley of a plurality of valleys of the particular ring to a corresponding peak of a plurality of peaks of the second adjacent ring.

10. The stent of claim 9, wherein a particular connecting strut of the second plurality of connecting struts is equidistant from a corresponding two connecting struts of the first plurality of connecting struts that are nearest to the particular connecting strut.

11. The stent of claim 1, wherein the first leg and the second leg of each of the plurality of skewed v-shaped elements of each of the plurality of rings have respective lengths such that there is a group of v-shaped elements that have corresponding apices aligned with each other in a direction that is parallel to a longitudinal axis of the stent.

12. The stent of claim 1, wherein the main body further comprises a second plurality of rings that form a second helix.

13. The stent of claim 1, the end ring comprising a plurality of tear drop shaped elements.

14. The stent of claim 13, wherein the transition region connects a peak of a tear drop shaped element of the plurality of tear drop shaped elements of the end ring to the main body.

15. The stent of claim 1, further comprising:

a second end ring positioned to an opposite side of the main body from the end ring;

wherein each of the plurality of rings of the main body is angled with respect to the end ring and the second end ring.

16. The stent of claim 15, wherein a width direction of an end of the end ring and a width direction of an end of the second end ring are perpendicular to a longitudinal axis of the stent.

17. The stent of claim 15, further comprising:

a second transition region for connecting the second end ring to the main body.

18. The stent of claim 1, further comprising:

a plurality of connecting struts extending between rings of the plurality of rings, each of the plurality of connecting struts arranged parallel to a longitudinal axis of the stent.

19. The stent of claim 1, wherein the length of the gap is less than a length of a third strut and greater than a length of a second strut; and the gap is between the second strut and the third strut.

20. The stent of claim 1, wherein the length of the gap being less than a length of a second strut and greater than a length of a first strut; and the gap is between the first and second struts.

* * * * *